United States Patent [19]

Timonen et al.

[11] Patent Number: 5,366,755
[45] Date of Patent: Nov. 22, 1994

[54] FOODSTUFFS CONTAINING NOVEL DEGRADED CELLULOSE DERIVATIVES

[76] Inventors: Maritta Timonen, Kantelettarentie 8E 57, Helsinki, Finland; ChoKyun Rha, 285 Commonwealth Ave., Boston, Mass. 02114; Timo Vaara, It. Puistot 16 L 14, Helsinki, Finland; Lindsey Bagley, 4, Barn Close, Maidenhead, Berkshire; Sarah Bosdet, 45, All Saints Close, Wokingham, Berkshire, both of England; Michael Lindley, 17, Highway, Edgecomb Park, Crowthorne, Berkshire, England; Tarja Lahtinen, Myllykalliontie 2 L 32, 00200 Helsinki, Finland; Marja Turunen, Aino Acktentie 10 A 7,, 00400 Helsinki, Finland; Martti Vaara, Aino Acktentie 10 A7, 00400 Helsinki, Finland

[21] Appl. No.: 743,152

[22] Filed: Aug. 9, 1991

Related U.S. Application Data

[63] Continuation-in-part of Ser. No. 309,387, Feb. 10, 1989, abandoned, Ser. No. 370,629, Jun. 23, 1989, abandoned, Ser. No. 730,029, Jul. 12, 1991, abandoned, Ser. No. 464,291, Jan. 12, 1990, abandoned, and Ser. No. 565,346, Aug. 10, 1990, abandoned.

[30] Foreign Application Priority Data

Aug. 9, 1990 [GB] United Kingdom ............... 9017452.5

[51] Int. Cl.⁵ .............................................. A23G 3/00
[52] U.S. Cl. .................................... 426/658; 426/48; 426/804
[58] Field of Search ............... 426/549, 531, 658, 48, 426/659, 660, 804, 601, 603; 536/56, 84, 85, 86, 88, 89; 127/37

[56] References Cited

U.S. PATENT DOCUMENTS

| | | | |
|---|---|---|---|
| 3,023,104 | 2/1962 | Battista | 99/1 |
| 3,397,198 | 8/1968 | Greidinger et al. | 260/212 |
| 3,418,133 | 12/1968 | Nijhoff | 99/1 |
| 3,591,457 | 7/1971 | Bender | 195/33 |
| 3,600,186 | 8/1971 | Mattson | 99/1 |
| 3,728,331 | 4/1973 | Savage | 260/231 R |
| 3,890,300 | 6/1975 | Huchette et al. | 260/233.3 |
| 3,986,890 | 10/1976 | Richter et al. | 127/38 |
| 4,011,392 | 3/1977 | Rudolph et al. | 536/108 |
| 4,048,433 | 9/1977 | Burns et al. | 536/99 |
| 4,281,063 | 7/1981 | Tsao et al. | 435/99 |

(List continued on next page.)

FOREIGN PATENT DOCUMENTS

| | | |
|---|---|---|
| 0149258 | 7/1985 | European Pat. Off. . |
| 0228951 | 7/1987 | European Pat. Off. . |
| 0231729 | 8/1987 | European Pat. Off. . |
| 2167986 | 1/1973 | France . |
| 2218882 | 9/1974 | France . |
| 667864 | 11/1938 | Germany . |
| 1668552 | 3/1972 | Germany . |
| 2324470 | 12/1973 | Germany . |
| 423225 | 4/1967 | Switzerland . |
| 594053 | 12/1977 | Switzerland . |
| 277111 | 9/1927 | United Kingdom . |
| 953944 | 1/1963 | United Kingdom . |
| 1122006 | 10/1965 | United Kingdom . |
| 1122965 | 4/1967 | United Kingdom . |
| 1495806 | 12/1977 | United Kingdom . |

OTHER PUBLICATIONS

H. Steege et al., "Microcrystalline cellulose powders . . . ", *Tappi*, vol. 61, pp. 101–105 (May 1978).

(List continued on next page.)

*Primary Examiner*—Donald E. Czaja
*Assistant Examiner*—Leslie Wong

[57] ABSTRACT

A degradation product of a polysaccharide derivative comprising a mixture of oligomers of the polysaccharide derivative, the majority of said oligomers having a molecular weight such that the oligomer conforms to a rod-like configuration.

14 Claims, 6 Drawing Sheets

U.S. PATENT DOCUMENTS

| | | | |
|---|---|---|---|
| 4,314,854 | 2/1982 | Takagi | 127/37 |
| 4,316,748 | 2/1982 | Rugg et al. | 127/37 |
| 4,316,982 | 2/1982 | Holst et al. | 536/88 |
| 4,421,856 | 12/1983 | Muller et al. | 435/161 |
| 4,427,584 | 1/1984 | LeGrand et al. | 260/124 R |
| 4,427,778 | 1/1984 | Zabriskie | 435/277 |
| 4,470,851 | 9/1984 | Paszner et al. | 127/37 |
| 4,517,204 | 5/1985 | Mottur et al. | 426/94 |
| 4,664,717 | 5/1987 | Young | 127/37 |
| 4,681,935 | 7/1987 | Forss et al. | 536/56 |
| 4,699,124 | 10/1987 | Nagle | 127/37 |
| 4,701,445 | 10/1987 | Shull | 514/57 |
| 4,831,127 | 5/1989 | Weibel | 536/56 |
| 4,839,088 | 6/1989 | Young | 252/183.13 |
| 4,842,877 | 6/1989 | Tyson | 426/271 |
| 4,859,474 | 8/1989 | Neidleman et al. | 426/28 |
| 4,871,571 | 10/1989 | Jensen et al. | 426/548 |
| 4,908,067 | 3/1990 | Just | 127/37 |
| 4,927,654 | 5/1990 | Barnett et al. | 426/548 |
| 4,959,466 | 9/1990 | White | 536/119 |

OTHER PUBLICATIONS

M. Chetkarov et al., "Kinetics of Enzymatic Hydrolysis of Carboxymethylcellulose", *Monatshefte fur Chemie*, 117, 1021–1026, (1986).

M. Chetkarov et al., "Kinetics and Mechanism of the Hydrolysis of Carboxymethylcellulose . . . ", *Monatshefte fur Chemie*, 116, 1433–1445 (1985).

B. Henrissat et al., "Synergism of Cellulases From Trichoderma Reesie . . . ", *Bio/Technology*, vol. 3, 722–726 (Aug. 1985).

N. Cauchon et al., "Effect of Dilution on Carboxymethylcellulose and Xylanase Assays", *Biotechnology and Bioengineering*, vol. XXVI, pp. 988–991 (1984).

S. S. Bhattacharjee et al., "Enzymatic Degradation of Carboxymethylcellulose and Other Cellulose Derivatives", *J. Polymer Sci.: Part C*, No. 36, pp. 509–521 (1971).

M. G. Wirick, "A Study of the Enzymatic Degradation of CMC and Other Cellulose Ethers", *Journal of Polymer Science: Part A-1*, vol. 6, 1965–1974 (1968).

Daicel Chemical Industries, *Chemical Abstracts*, 101:56734P (1984).

V. Gasciolli et al., "Viscous Properties and Molecular Characterization . . . ", *Journal of Biotechnology*, 19 (1991) pp. 193–202.

FOODSTUFFS CONTAINING NOVEL DEGRADED CELLULOSE DERIVATIVES

CROSS-REFERENCE TO RELATED APPLICATIONS

This is a continuation-in-part of all of U.S. patent application Ser. No. 07/309,387 filed Feb. 10, 1989 now abandoned, U.S. patent application Ser. No. 07/370,629 filed Jun. 23, 1989 now abandoned, U.S. patent application Ser. No. 07/730,029 filed Jul. 12, 1991 now abandoned, U.S. patent Application Serial No. 07/464,291 filed Jan. 12, 1990 now abandoned and U.S. patent application Ser. No. 07/565,346 filed Aug. 10, 1990 now abandoned, the contents of each application is hereby expressly incorporated by reference.

The contents of applicants' co-pending related application U.S. application Ser. No. 07/566,013 filed Aug. 10, 1990 now abandoned entitled "Paper Composition and Methods Therefor" and U.S. patent application Ser. No. 07/567,045 filed Aug. 10, 1990 now abandoned entitled "Polysaccharide Article and Uses Therefor", also are expressly incorporated by reference.

To the extent certain additional subject matter herein corresponds to the contents of British Patent Application No. 9017452.5 filed Aug. 9, 1990, priority thereof is also hereby claimed and the contents of the British patent application also are expressly incorporated by reference.

FIELD OF THE INVENTION

This invention relates to novel degradation products of polysaccharide derivatives, processes for their production and novel products and processes utilizing such novel degradation products. The invention includes substitution of novel degradation products in food products for a substantial portion of the normal fat, sugar, carbohydrate or other high caloric content of a food product.

The invention also relates to the production and use of a new food ingredient which is fat-free having properties akin to the normal fat, sugar or carbohydrate content of a conventional foodstuff. Such properties of the new ingredient imparts an acceptable eating quality to conventional food recipes, such that it can be used as a component in making food or can be used to replace, in part or full, the ordinary fat or carbohydrate content in various food products.

BACKGROUND OF THE INVENTION

Cellulose derivatives such as carboxymethylcellulose, methylcellulose, methylethylcellulose, hydroxypropylmethylcellulose and hydroxypropylcellulose are non-caloric (non-metabolizable by humans or intestinal flora in human beings), odorless, tasteless water-soluble polymers derived from cellulose. These cellulose derivatives may act as thickeners, binders, stabilizers, suspending agents or flow control agents. They form films resistant to oils, greases and organic solvents. They dissolve rapidly in cold and hot water and are physiologically inert. In theory, the non-caloric nature of cellulose derivatives would suggest that they might be used as filler materials or substitutes for fat, sugar, carbohydrate or other high calorie components of normal food products. However, the simple substitution of such non-toxic non-caloric substances for a high calorie food component, is not practicable because any substantial substitution of a normal food ingredient will typically alter one or more of the color, volume, texture, structure, mouthfeel, odor or flavor of the food to such an extent as to render the food product unacceptable to a consumer.

Degradation of cellulose derivatives is normally considered undesirable and to be avoided. Cellulolytic and viscosity reducing treatments on cellulose derivatives have been deliberately avoided in the past and high molecular weight products deliberately produced. Indeed, non-degraded cellulose derivatives have been incorporated into food stuff compositions as disclosed in U.S. Pat. No. 4,214,009 to Chang.

Enzymatic hydrolysis of cellulose derivatives have been studied in the past in the context of synergism studies among combinations of enzymes, the possible indexing of substituent distribution patterns, the effect of various substituents on enzymatic hydrolysis and the like. Such studies have been published in the following: Chouchon et al., *Biotech. Bioeng.*, Vol. 26, pp. 988–991 (1984); Henrissat et al., *Biotechnology*, Vol. 3, pp. 722–726 (1985); Chetkarov et al., *Monatshefte Fur Chemie*, Vol. 116, pp. 1433–45 (1985); Chetkarov et al., *Monatshefte Fur Chemie*, Vol. 117, pp. 1021–1026 (1986); Wirick, *J. Polym. Sci.*, Part A-1, Vol. 6, pp. 1195–1974 (1968); Bhattacharjee, *J. Polym. Sci.*, Part C, Vol. 36, pp. 509–521 (1971). Reduction of chain length have also been studied. Almin et al., *Arch. Biochem. Biophy.*, pp. 124, 129 (1968); Ghose, *Biotech. Bioeng.*, Vol. 11, pp. 239 (1969).

Numerous studies throughout the world have shown a link between a fatty diet high in cholesterol, and heart diseases. Also, because of its high energy content (about 9 kcalories/g) high fat consumption may cause obesity and its associated problems. It is recommended (by e.g. The American Heart Association) that fat consumption should be reduced so that no more than 30% of caloric energy is derived from fat. It also has been recommended that an increased proportion of calorie intake should be obtained from complex carbohydrates rather than fat. Fat in the diet should thus be partially omitted or substituted. However, fat endows desirable eating qualities (e.g. taste, mouthfeel, aroma, consistency) and consumers are used to and enjoy the properties that fat lends to food. So substitution of fat with a non-fat substance that is fat-free but has fatty consistency and mouthfeel would be an attractive approach to this problem.

The production of different types of starch derivatives has been described, e.g. in Radley, J. A. *Starch And Its Derivatives*, 4 ed. [p. 382] 1968 and in Rutenberg et al., *Starch: Chemistry and Technology*, 2ed., pp. 311–88 (1984). Derivatives such as oxidized starches, cross-linked starches, starch ethers and cationic starches are discussed in the foregoing. One or more of the inventors herein have also shown the production and use of higher molecular weight polysaccharides, including starch and cellulose derivatives, in a variety of different applications in U.S. Pat. Nos. 4,810,646; 4,851,393; 4,749,620; 4,744,933; 4,739,693; 4,732,205; 4,119,783; 4,666,492.

Carboxymethyl starch (CM starch) is an ether type starch derivative typically prepared by the reaction of chloroacetic acid on starch in the presence of alkali. The sodium salt of CM starch, which occurs also under the name sodium starch glycolate, is used as a disintegrant in pharmaceutical tablets. Other proposed or actual usages are, e.g. components of absorbents, adhesives, medical poultices, thickening agents, stabilizers, papermaking, coating and pulp refining. CM amylose has been suggested to be used to lower the blood sugar level or as blood volume expander. It has been used as a substrate when studying the kinetics of amylases. CM starch is insoluble in cold water, but it has high water absorption properties such that CM starch particles swell to several times their original volume.

Maltodextrin, enzymatically hydrolysed starches, are commercially available. However, these products are less preferable.

There are also some new developments in the area of low-calorie fat mimetics that have been recently approved or are awaiting regulatory approval. They have been made, e.g. by modifying natural proteins physically or by modifying sucrose chemically. However, many of these compounds have functional limitations.

SUMMARY OF THE INVENTION

As to cellulose and starch based materials, the terms polysaccharide and polysaccharide derivative, as used herein, are intended to refer only to cellulose and starch polymers which are substituted with substituents such as carboxymethyl, hydroxypropyl and other substituents as discussed herein. As to polymers or oligomers other than cellulose or starch based materials, the terms polysaccharide and polysaccharide derivative include polymers of sugar monomers such as glucose, galactose, mannose, fructose, etc. which are either substituted or unsubstituted.

The invention pertains to a degradation product of a polysaccharide or polysaccharide derivative which is useful in foodstuff compositions. The preferred polysaccharide derivative starting material is a cellulose derivative and the preferred mode of degradation is enzymatic degradation.

In a first embodiment the degradation product of the polysaccharide derivative is a mixture of oligomers having a molecular weight such that the oligomers conform to a rod-like configuration. The conformation of the oligomers to rod-like configurations allows the oligomers to align with one another as depicted in FIG. 6.

In a second embodiment, the degradation product of the polysaccharide derivative is a mixture of oligomers having a Mark-Houwink exponent (a) of at least 1.5 at an NaCl concentration of from about 0.005N to about 0.5N. The Mark-Houwink exponent (a), a parameter used to study the chain conformation of polymers, will be discussed in detail below.

In a third embodiment, the degradation product of the polysaccharide derivative is a mixture of oligomers having an average degree of polymerization ("DP") in the range of about 3 to about 500. The preferred average degree of polymerization is from about 3 to about 300, more preferably from about 5 to about 100, and most preferably from about 5 to about 50.

The invention further pertains to the use of the above-described degradation products in foodstuff compositions. The invention contemplates removing all or a portion of an ingredient contained in the composition of a foodstuff, e.g. a fat ingredient, and substituting therefor a mixture of oligomers produced according to the invention. A removed fat ingredient may be a saturated triglyceride of a fatty acid, phospholipid and cholesterol containing materials such as butter, oil, and mayonnaise. The mixture of oligomers produced according to the invention also may be used to replace all or a portion of the carbohydrate content contained in a foodstuff. Typical carbohydrates which may be replaced are starch, dextrin, sucrose, glucose, maltose or fructose found in foodstuffs such as corn or wheat flour, corn meal, syrup, molasses and the like. Oils and lipids which are normally found in foods such as unsaturated triglycerides, phospholipids and lecithin also may be replaced by the new ingredient of the invention.

The invention therefore provides for a method of preparing a low calorie food product comprising replacing at least part of the high calorie components of a foodstuff with the above-described degradation products. Preferably, the new low calorie food ingredient can be substituted for all or at least about 10% of the normal fat or carbohydrate content of a conventional food recipe.

Typical embodiments of the invention are disclosed for cake, icing, butter, spread (margarine), marzipan and mayonnaise which normally comprise a relatively high content of caloric fat, sugar or carbohydrate ingredient. The high calorie ingredient is replaced, in whole or in part, with a mixture of oligomers derived from a degraded polysaccharide derivative.

The aforesaid degraded polysaccharide derivative, for example cellulose derivatives, may be used in extruded snacks, i.e. low moisture steam expanded foodstuffs having an essentially starch matrix, but which may include other ingredients for textural or flavour purposes. Snacks include many well known types of extruded or moulded foodstuff, including crisp breads, biscuits and cereal based products. The presence of the cellulose derivative in such products confers a novel glass type texture which confers crispness on the product without the need for deep fat frying or inclusion of a high fat content in the product itself. The fat content of such snacks can therefore be reduced with little or no compromise in overall quality and customer acceptability of the product. For example, snacks based on maize meal can be produced in accordance with the invention containing 0.05 to 5% by weight of the cellulose derivative, preferably 1 to 2% by weight. As compared with maize based snacks not containing the cellulose derivative, the snacks in accordance with the invention have a lighter structure, a crisp crunchy texture without frying, and less stickiness.

The cellulose derivatives may also be incorporated advantageously into gelled starch food products having a high water content, e.g. a batter, which is a starch based gel of high water content which is cooked typically by immersion in hot fat to give a product having a crisp outer surface with a moist food inside. Inclusion of the cellulose derivative leads to a reduction in the required cooking (frying) time, better water retention of the cooked foodstuff combined with a lower uptake of the cooking fat, a crisper product which retains its crispness for prolonged periods, a better appearance and improved customer acceptability. Moreover, the useful like of the cooking oil is prolonged. Preferably the batter mix contains from 1 to 5%, preferably about 2%, by weight of the cellulose derivative.

DETAILED DESCRIPTION OF THE INVENTION

Figure 1:
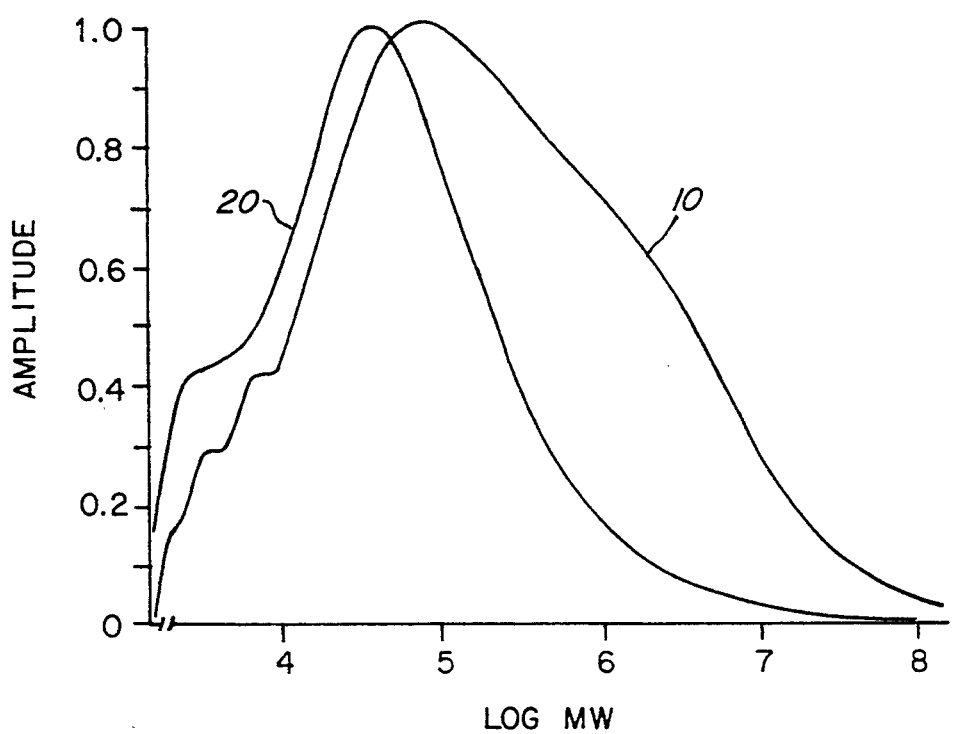
FIG. 1 shows molecular weight distribution patterns of a methylcellulose and its hydrolysate as described in Example 2a herein.

This invention pertains to degradation products of polysaccharide derivatives, their manufacture, and their use in foodstuff compositions. The degradation products of this invention can replace a high caloric ingredient in a foodstuff composition producing a lower caloric foodstuff composition.

In a first embodiment, the degradation product of the polysaccharide derivative is a mixture of oligomers of the polysaccharide, a majority of the oligomers having a molecular weight such that the oligomer conforms to a rod-like configuration. Examples of oligomers in a rod-like configuration are depicted in the second column (Low Molecular Weight) of FIG. 6.

The term degradation product for the purposes of this invention involves any product resulting from the degradation of a polysaccharide derivative. The degradation process may be enzymatic, chemical, physical, or mechanical.

In an enzymatic degradation process, the enzyme preparation typically is selected depending upon the polysaccharide derivative desired to be degraded. For example, in the case of starch derivatives, enzymes such as amylases, pullanases and mixtures thereof are suitable. An enzyme preparation useful for degrading cellulose derivatives typically comprises a cellulase or modified cellulase. The cellulase may be modified to remove or prevent the formation of mono- and disaccharides producing enzymes in the cellulase preparation. This can be done by genetic alteration of the microorganism from which the cellulase preparation is prepared which preferably is a microorganism selected from the group of Trichoderma, Aspergillus and Penicillium. Most preferably a cellulase preparation is derived from *Trichoderma reesei* from which at least one of beta-glucosidase and cellobiohydrolase activities have been removed. A most preferred cellulase comprises endo-1,4-beta-glucanase.

Other exemplary enzymes for use in degrading certain polysaccharide derivatives are pectinases, lyases, xanthanases, chitinases, lysozymes and laminarinases.

Apart from enzymatic treatments, a polysaccharide derivative may be degraded by hydrolyzing the polysaccharide derivative with a solution of an acid or base. Typical acid treatment solutions may contain sulphuric acid, hydrochloric acid, phosphoric acid, nitric acid or mixtures of two or more of the foregoing. Typical base solutions may contain a hydroxide ion containing or producing material such as an alkali hydroxide (e.g. sodium hydroxide), ammonium hydroxide, and mixtures of two or more of the foregoing. The concentration of the acid or base in the treatment solution and the treatment time and temperature may vary depending on the degree of degradation of the polysaccharide derivative which is desired. The person skilled in the art will recognize that higher acid or base concentrations, treatment times and treatment temperatures will generally result in a higher degree of degradation of the polysaccharide derivative (i.e. an oligomeric product mixture having a lower average DP and molecular weight). Lower acid or base concentrations, shorter treatment times and lower temperatures will generally produce oligomeric product mixtures of higher average DP and molecular weight.

A selected polysaccharide derivative may also be degraded by oxidation with such agents as oxygen or hydrogen peroxide in basic solution or with ozone. Such oxidative treatments and reaction conditions are well known in the art. Gaseous agents such as oxygen or ozone would typically be bubbled continuously through the solution for a suitable time and at a suitable temperature. An oxidative treatment with peroxide may comprise treating a selected cellulose derivative with a solution of hydrogen peroxide of suitable concentration and at a suitable temperature to obtain an oligomeric mixture having a preferred DP range.

The invention further contemplates oligomeric mixtures produced by physical (mechanical) depolymerization methods such as by subjecting a solution of a selected polysaccharide derivative to treatment with relatively high frequency sound waves with a sonicator. Other physical treatments well known in the art such as chopping or shearing, for example, with a high speed mixer or homogenizer may be employed to effect depolymerization.

Whatever conventional chemical (hydrolyric, oxidative or otherwise) or physical treatments are employed, the conditions and the degree of treatment are selected such that the oligomeric mixture resulting from the initial treatment has an average DP of between 3 and 500, and contains less than about 25% by weight of mono- and disaccharides and most preferably less than about 10% by weight of mono- and disaccharides.

Polysaccharide derivatives having a polymer backbone including one or more sugar monomers such as glucose, galactose, arabinose, mannose, fructose, rhamnose, and xylose may be suitable starting materials. Such polymer backbones may be branched or straight. Examples of such polysaccharide derivatives are starch derivatives, cellulose derivatives, pullulan, pustulan, laminarin, scleroglucan, carragenan, alginate, guar gum, gum arabic, inulin, pectin, whelan, rhamsan, gellan, xanthan, zooglan, methylan, chitin, cyclodextrin and chitosan. Typical derivative substituents which are substituted onto the simple sugars of the backbones of such polysaccharides are one or more of sulfate, amino, carboxylic acid (such as in carragenan, alginate, pectin), carboxylic acid ester, pyruvic acid, pyruvate (such as in pectin, xanthan gum, zooglan, methylan), carboxymethyl, hydroxypropyl, hydroxyethylpropyl, methyl, methylethyl, hydroxypropylmethyl, hydroxypropylethyl, hydroxyethyl, hydroxyethylmethyl and the like.

Preferably the polysaccharide derivative starting material has a degree of substitution of between about 0.1 to about 3.0. "Degree of substitution" refers to the number of derivative groups (e.g. carboxymethyl, hydroxypropyl) per monomer units in the polysaccharide backbone (branched or straight chain). A degree of substitution of 0.2 would mean, for example, that there is about one derivative substituent per every 5 monomer units in the polysaccharide polymer. A degree of substitution of three (3) would mean there are three derivative substituents per every monomer unit in a polysaccharide chain.

In the case of starch, The derivative substituents are typically bonded to a glucose monomer unit at the 2, 3 and 6 positions. Most typically a starch starting material comprises between about 1% to 85% amylose and about 15% to 99% amylopectin.

Carboxymethyl ("CM") starch can be hydrolyzed enzymatically to produce CM starch hydrolysates. Suspensions or gels prepared from these hydrolysates have fat-like properties and are similar to fat in mouthfeel and in handling properties. CM starch is easily hydrolyzed with commercial amylases, and even mild hydrolysis may produce preparations suitable for use as fat replacers. CM starch can be made from various sources of starch including wheat, rice, tapioca, corn and potato starch and other major grain or plant starches. Potato starch, a typical starting material, contains about 20% amylose (DP of about 3,000) and about 80% amylopectin (DP of about 2,000,000). The derivatives of this invention include hydroxypropyl, carboxymethyl methylethyl and hydroxyethyl starches.

Cellulose derivatives are commercially available. Such exemplary products as methylcellulose (MC, Methocel MC, 64630, Fluka Chemie AG, CH-9470 Buchs, Switzerland), hydroxypropylmethylcellulose (HPMC, H-9262, Sigma Chem. Co., St. Louis, Mo.) and carboxymethyl cellulose (CMC 7MFD, Blanose, Hercules Chem. Co., 92507 Rueil-Malmaison Ceder, France) all have a degree of substitution between 0.1 and 3. Hydroxypropyl celluloses also are commercially available and suitable for use in producing a degraded polysaccharide derivative according to the invention.

For purposes of this invention, the term oligomer is a polymer of the polysaccharide derivative containing less monomer units than the starting polysaccharide derivative. For example, the oligomer may contain five to fifty sugar units wherein the polysaccharide or its derivative starting material has a far greater number of sugar units.

The language "conforms to a rod-like configuration" is intended to include the situation wherein the oligomer is in a substantially straight configuration and not in a coiled configuration. A group of oligomers in a rod-like configuration are depicted in the second column (Low Molecular Weight) of FIG. 6. Polymers have distinct solution properties and conform to a rod-like confirmation below a certain molecular weight.

The Mark-Houwink equation may be used to study the chain conformation of a polymer. The Mark-Houwink equation is as follows: $[\eta] = KM^a$ wherein the Mark-Houwink exponent, a, is indicative of the conformation of a polymer chain in a solution. The conformation of a polymer chain in a solution may be classified as an 1) impermeable dense sphere, 2) random coil, e.g. semi-permeable or free draining, and 3) rodlet or rod-like. Mark-Houwink exponents of 0.002 to about 0.5 correspond to dense spheres, exponents of about 0.5 to about 0.8 correspond to semi-permeable random coils, exponents of 0.8 to about 1.2 correspond to free draining random coils and exponents of about 1.2 to about 2 correspond to rodlets or rod-like oligomers or polymers. The determination of Mark-Houwink exponents is described in detail in Example 6 below.

In an embodiment of this invention, the degradation product of the polysaccharide derivative comprises a mixture of oligomers of the polysaccharide having a Mark-Houwink exponent of at least 1.5 at an NaCl concentration of about 0.005N to about 0.5N. The NaCl concentration range typically is used when measuring the Mark-Houwink exponents. The salt content of foodstuffs may typically fall into this range.

In another embodiment, the degradation product of the present invention is a mixture of oligomers of a polysaccharide having an average degree of polymerization in the range of about 3 to about 500 and a molecular weight of 500 to 60,000. The average degree of polymerization was calculated by determining the average molecular weight of the oligomer mixture and dividing the average molecular weight by the known molecular weight of the respective monomer.

Enzyme Preparations for Use With Cellulose Derivatives

Enzymes which may be used in some embodiments of this invention are various food-grade cellulase preparations. They can be produced from a multitude of different microorganisms such as strains of Trichoderma, Aspergillus, Penicillium, etc. A selected microorganism strain is grown by conventional means in a medium containing food grade materials such that the cellulases are produced, the microorganism is separated from the medium, the medium is collected and typically concentrated and dried. These enzymes can be used as such or in mixtures and they can be modified in many different ways known to the man skilled in the art. A most preferred enzyme preparation is produced from *Trichoderma reesei*, from which preparations the beta-glucosidase and/or the cellobiohydrolase activities are removed chromatographically or genetically. Beta-glucosidase and/or cellobiohydrolase activities preferably are removed from the selected cellulase preparation so as to prevent the degradation of the cellulose derivative into mono- and disaccharides. Genetic alteration of the appropriate enzyme producing microorganism may be effected with radiation or mutagenic chemical agents (or by gene inactivation by recombinant DNA methods) so as to disenable production of beta-glucosidase and cellobiohydrolase by the microorganism. Cellulase preparations suitable for use herein are, e.g., the commercially available cellulase preparations designated as the Econase series as produced by Alko Ltd., Helsinki Finland.

Starting Materials

Preferred cellulose derivatives for use herein are carboxymethyl-, methyl-, methylethyl-, hydroxypropylmethyl- or hydroxypropylcellulose and any combinations thereof. The invention is not limited to the use of these cellulose derivatives.

General Preparation of a Typical Cellulose Derivative Hydrolysate

In one embodiment of the invention, cellulose derivative hydrolysates may be prepared from soluble cellulose derivatives as defined above by an enzymatic hydrolysis utilizing a cellulase preparation having endo-1,4-beta-glucanase as the sole active hydrolytic agent such that only insignificant amounts of mono- and disaccharides which are absorbed in human intestine (e.g., glucose) or hydrolyzed by the intestinal bacterial flora (e.g., cellobiose), are produced. The average degree of polymerization (DP) of the oligomers formed by such a hydrolysis is greatly reduced relative to the starting material, and thus the viscosity of solutions of the hydrolysate is reduced significantly compared to the viscosity of solutions of the unhydrolysed cellulose derivatives. The specific conditions suitable for and the specific time sufficient to secure the desired hydrolysis may be readily determined for each selected cellulose derivative and each selected enzyme preparation.

Similarly in other embodiments of the invention where degradation is carried out using chemical or physical means, the viscosity of the resulting mixture is significantly reduced. Preferably in such embodiments, the treatment conditions are selected such that the resulting oligomeric mixtures contain less than about 25%, and most preferably less than about 10%, by weight of mono- and disaccharides.

Use of Oligomeric Mixtures Derived from Cellulose Derivatives

The degraded cellulose derivative products of the invention (and fractions thereof) dissolve rapidly in cold and hot water and are physiologically inert. In general, such initially formed oligomeric mixtures and selected fractions may act as thickeners, binders, stabilizers, suspending agents or flow control agents, or fillers in wide variety of applications. In food applications, an oligomeric mixture falling within a particular range of viscosities may be preferred in a particular food recipe insofar as it may be desirable to obtain an end product which resembles the eating quality of the normal recipe containing the normal relatively high level of fat or other high calorie ingredients in a particular foodstuff.

The following examples 1-4 set forth typical exemplary routines for preparing a cellulase and various cellulose derivative hydrolysates therefrom.

EXAMPLE 1

Typical Cellulase Preparation

The beta-glucosidase activity was removed by ion exchange chromatography from the commercially available cellulose preparation, Econase CE, as so designated by Alko Ltd., Helsinki, Finland which was produced from a strain of *Trichoderma reesei*. The cellulase preparation (column A, Table 1) was passed through a cation exchange column (S-Sepharose FF, Pharmacia, LKB Biotechnology AB, Uppsala, Sweden) which was equilibriated with 50 mM sodium acetate pH 3.8 equilibrium buffer. The unbound protein (including oligomer producing endoglucanases) was washed out with the equilibrium buffer (column B, Table 1). Beta-glucosidase activity remained bound to the column and could be separately eluted with 1M NaCl.

TABLE 1

| | Relative Enzyme Activity (%) | |
|---|---|---|
| | A | B |
| | before ion exchange | after ion exchange |
| Enzyme | procedure | procedure |
| Beta glucosidase | 100 | 0 |
| endo-1,4,-beta-glucanase | 100 | 70 |

Endo-1, 4- beta-glucanase and beta-glucosidase activities were measured as described by Bailey & Nevalainen (1981): *Enzyme Microb. Technol.* 3: 153–157, the contents of which are hereby incorporated by reference. The relative enzyme activities reported in Table 1 of the Econase preparations before and after passage through an ion exchange column demonstrate the results of a typical means according to the invention of preparing an essentially beta-glucosidase free preparation for use in producing the oligomeric hydrolysates contemplated by the invention.

Although Table 1 reports relative enzyme activities, the absolute amount of enzyme used in any particular example is hereafter reported in terms of the amount of enzyme activity of the enzyme employed according to the universal activity unit of nano-katal (nkat) which stands for that amount of enzyme which produces one nanomole of reaction product in one second. The method of Bailey et al., *Enzyme Microb. Technol.*, Vol. 9, pp. 153–157 describes how such measurements of enzyme activity can be made using glucose as a standard.

EXAMPLE 2

Cellulose Derivative Enzymatic Hydrolyses a. Methylcellulose Hydrolysate 30 g of methylcellulose (MC, Methocel MC, 64630, Fluka Chemie AG, CH-9470 Buchs, Switzerland) was mixed in 3 l of water and the pH of the solution was adjusted to 5.5 with 15% phosphoric acid and the temperature was raised to 40° C. 0.3 ml of the enzyme preparation having a total endo-1, 4 beta-glucanase activity of 1680 nkat from which the beta-glucosidase activity was removed chromatographically (as described in Example 1) was added to the solution. After hydrolysis for 24 hours the enzyme was inactivated by heating (90° C., 15 min.). The hydrolysate solution was subsequently cooled and freeze-dried.

The hydrolysate product contained less than 0.5% by weight of glucose and cellobiose.

The molecular weight distribution patterns of methylcellulose, curve 10, and its hydrolysate, curve 20, are shown in FIG. 1.

The molecular weight distributions of the cellulose derivatives and their hydrolysates were determined by HPLC using a gel filtration column (TSK gel G2500PW, Toyo Soda Manufacturing Co., Ltd., Japan) with a refractive index detector (HP 1037 A) and Pharmacosmos Dextran Standards (Pharmacosmos, DK-4130, Viby Sj., Denmark). The eluent was 0.5M sodium chloride.

b. Hydroxypropylmethylcellulose Hydrolysate 20 g of hydroxypropylmethylcellulose (HPMC, H-9262, Sigma Chemical Company, St. Louis, Mo., U.S.A.) was mixed in 1 l of water and the pH of the solution was adjusted to 5.5 with 15% phosphoric acid and the temperature was raised to 40° C. 0.24 ml of the enzyme preparation having a total endo-1, 4 beta-glucanase activity of 1340 nkat from which the beta-glucosidase activity was removed chromatographically (as described in Example 1) was added to the solution. After two hours another 20 g of hydroxypropylmethylcellulose was added to the solution. After the hydrolysis of 22 hours the enzyme was inactivated by heating (90° C., 15 min.). Finally the hydrolysate solution was cooled and freeze-dried.

The product contained less than 0.05% by weight of glucose and cellobiose.

Figure 2:
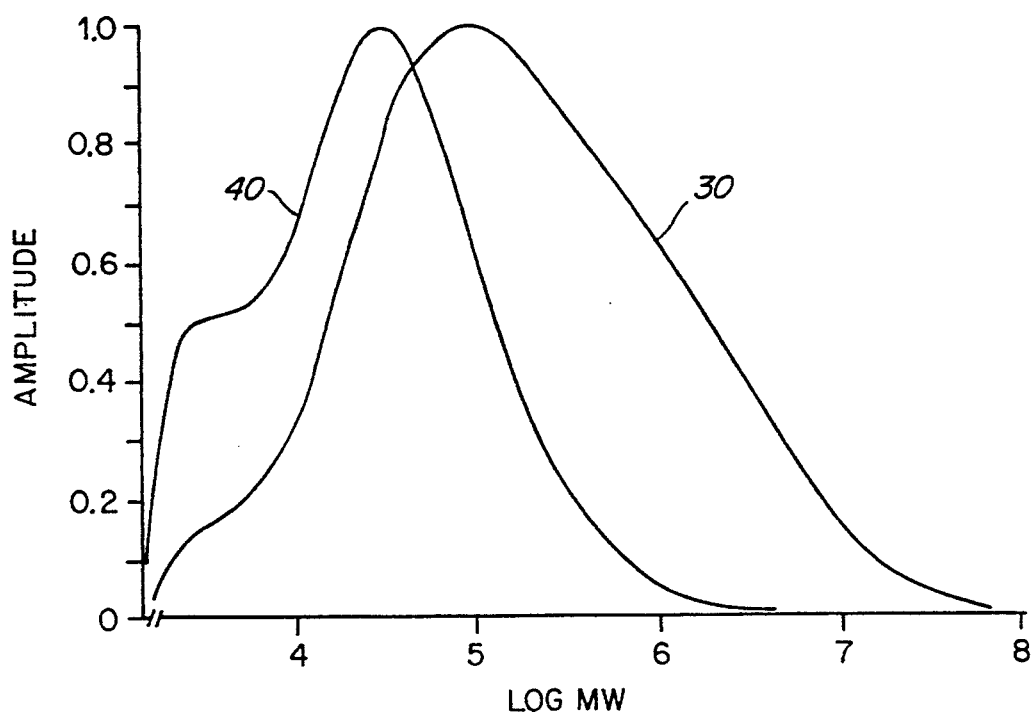
FIG. 2 shows molecular weight distribution patterns of hydroxypropylmethylcellulose and its hydrolysate as described in Example 2b herein.

The molecular weight distribution patterns of the hydroxypropylmethylcellulose, curve 30, and its hydrolysate, curve 40, are shown in FIG. 2. The molecular weight distribution pattern was determined as described in Example 2A.

c. Carboxymethylcellulose Hydrolysate (i) Hydrolysis with *Trichoderma reesei* derived enzyme preparation 20 kg of carboxymethylcellulose (CMC 7MFD-type, a cellulose gum, also designated by the tradename Blanose and available from Hercules Chemical Company, 92507, Rueil-Malmaison Cedar, France; 7MFD designating a medium viscosity, food grade sodium carboxymethylcellulose having 7 out of 10 glucose units substituted with carboxymethyl) was mixed in 320 l of water and the pH of the solution was adjusted to 5.5 with 15% phosphoric acid and the temperature was raised to 40° C. 0.27 l of the enzyme preparation having a total endo-1, 4 beta-glucanase activity of 1,780,000 nkat from which the beta-glucosidase activity was removed chromatographically (as described in Example 1) was added to the CMC solution. After one hour another 20 kg of CMC was added to the solution. After hydrolysis of 23 hours the enzyme was inactivated by heating (90° C., 15 min.). Finally, the hydrolysis solution was concentrated by conventional evaporating and spray-drying.

The product contained less than 2% by weight of glucose and cellobiose. When the same hydrolysis was carried out with the original cellulase enzyme preparation of *Trichoderma reesei-fungus,* the amount of produced glucose and cellobiose was above 5% by weight.

Figure 3:
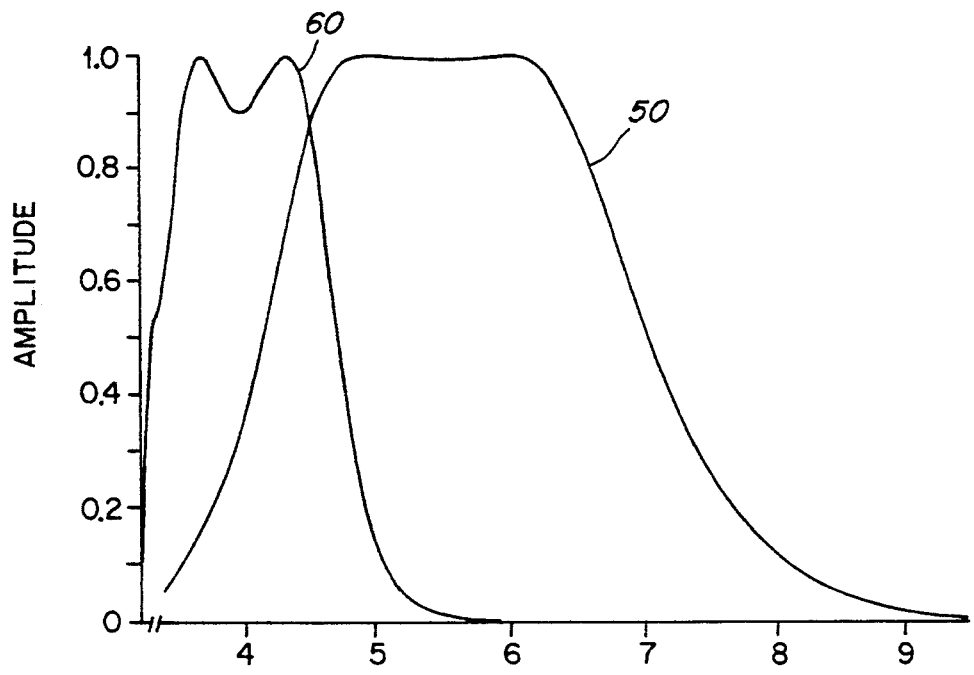
FIG. 3 shows molecular weight distribution patterns of a carboxymethylcellulose and its hydrolysate as described in Example 2c(i) herein.

The molecular weight distribution patterns of carboxymethylcellulose, curve 50, and its hydrolysate, curve 60, are shown in FIG. 3.

The molecular weight distribution pattern was determined as described in Example 2a.

(ii) Hydrolysis with Aspergillus and Penicillium derived enzyme preparations

The enzyme preparations selected were commercially available Cellulase AP 3 (Amano Pharmaceutical Co., Ltd., Nagoya, Japan) produced using an Aspergillus strain and Cellulase CP (Sturge Enzymes, North Yorkshire, England) produced using a Penicillium strain. Carboxymethylcellulose hydrolysates were prepared as described in Example 2c(i), except that 30 g of CMC-7MFD was used in 1 l of water, and the amounts of enzymes added were 0.028 g of Cellulase AP 3 (having a total endo-1, 4 beta-glucanase activity of 1350 nkat) and 0.048 g of Cellulase CP (having a total endo-1, 4 beta-glucanase activity of 1350 nkat). The viscosities and molecular weight distributions of the hydrolysates produced by either cellulase were similar (FIG. 3) to the hydrolysate produced with enzymes derived from *Trichoderma reesei.*

The viscosities of the various cellulose derivatives and their hydrolysates as described and prepared in Example 2 were measured using a Haake-Rotovisco viscometer with sensor systems NV (Karlsruhe, Federal Republic of Germany) (Table 2). The viscosities were measured in water solutions at 25° C. Table 2 sets forth the concentrations (by weight) of a variety of solutions all having the same viscosity.

TABLE 2

Concentrations of cellulose derivatives and their respective hydrolysates in solution all having a viscosity of 20 mPa.s (milli Pascals-second) at 25° C.

| Cellulose Derivative | Concentration (by weight) |
|---|---|
| Methylcellulose | 2% |
| Methylcellulose hydrolysate | 5% |
| Hydroxypropylmethylcellulose | 3% |
| Hydroxypropylmethylcellulose hydrolysate | 10% |
| Carboxymethylcellulose | 2% |
| Carboxymethylcellulose hydrolysate | 20% |

As the data in Table 2 indicates, the hydrolysate of a cellulose derivative has a substantially lower viscosity than an equal amount by weight in aqueous solution of the cellulose derivative itself. Thus, the hydrolysate can be incorporated into a foodstuff in substantially higher quantity as a fat or sugar substitute than the cellulose derivative itself without compromising the texture, volume, density or the like of the foodstuff.

EXAMPLE 3

A Fractionation of Carboxymethylcellulose Hydrolysate

Figure 4:
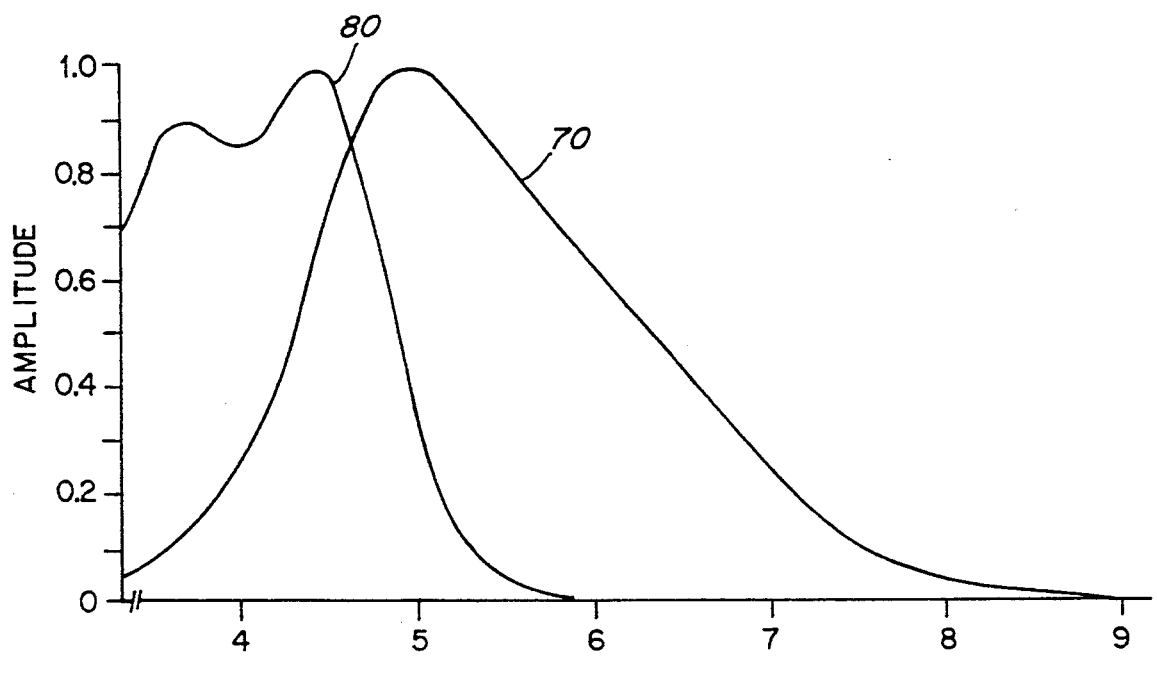
FIG. 4 shows molecular weight distribution patterns of a carboxymethylcellulose and its hydrolysate as described in Example 3 herein.
Figure 5:
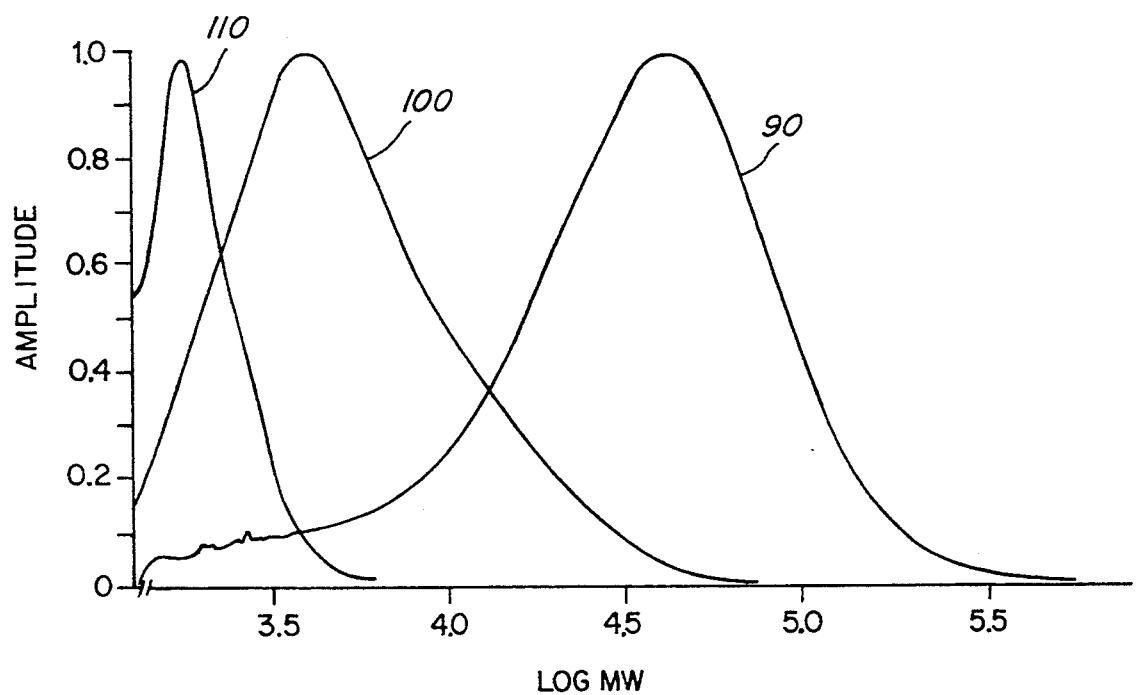
FIG. 5 shows molecular weight distribution patterns of selected fractions of the carboxymethylcellulose hydrolysate as described in Example 3 herein.

The carboxymethylcellulose hydrolysate was prepared as described in Example 2c(i), except that the raw material was CMC 7LFD (designating a low viscosity, food grade cellulose gum having 7 out of 10 glucose units substituted with carboxymethyl, designated under the tradename Blanose and available from Hercules Chemical Co., France) 1.6 kg CMC was used in 8 l of water and that the amount of enzyme added was 13.2 ml having a total endo-1, 4 beta-glucanase activity of 87,000 nkat. 5 ml of the hydrolysate (0.5 g of dry matter) was further fractionated into three fractions by gel permeation chromatography (Pharmacia K 26/100 -column, Sephacryl S-200 -gel, Pharmacia LKB Biotechnology AB, S-75182 Uppsala, Sweden). The eluent was distilled water, the flow rate was 14 ml/hour, and the fractionation process was carried out for 45 hours and fractions collected at intervals of 0.5 hours and pooled into three fractions (18 hours—26 hours, curve 90, 26 hours—32 hours, curve 100, and 32 hours—38 hours, curve 110, FIG. 5, respectively). The molecular weight distributions of carboxymethylcellulose, curve 70, carboxymethylcellulose hydrolysate, curve 80, and the three further fractions, curves 90, 100, 110, FIGS. 4, 5, were determined by HPLC as described in Example 2.

EXAMPLE 4

CMC Chemical Hydrolysis 2 g of carboxymethylcellulose (Blanose Cellulose Gum 7 LFD, Hercules Chemical Co., 92507, Rueil-Malmaison Cedar, France) was hydrolyzed for one hour in 100 ml of 1M sulphuric acid solution at 100° C.

After hydrolysis the solution was cooled to about room temperature, neutralized to about pH 6 with 25 ml of 25% (w/w) of NaOH solution and freeze-dried. This hydrolysis treatment produced a mixture of oligomers containing less than about 4% by weight of mono and disaccharides. The viscosity (and average DP) of this hydrolysate is similar to the viscosities (and average DP) of the hydrolysates produced by the enzymatic treatments described above utilizing enzymes derived from *Trichoderma reesei*.

Specific Exemplary Formulations Wherein High Caloric Ingredient is Reduced

As described below a variety of popular high calorie food recipes were modified by substituting certain amounts of various carboxymethylcellulose hydrolysates for a certain portion of the normal level of a high calorie component of the food recipes. With respect to the invention, it is to be understood that the replacement of a high caloric ingredient is not limited to any particular cake, spread, icing, mayonnaise or other food recipe as may be specifically set forth herein for purposes of example. The various carboxymethylcellulose hydrolysates employed as substitutes or additives in the food recipes described hereinafter are referred to as EP151, EP151-2, EP151-49, EP151-51 and EP151-52 and the methods for preparing same were as follows:

a. CMC Hydrolysate EP151 was prepared as described in Example 2c(i) hereinabove.

b. CMC Hydrolysate EP151-2

20 kg of carboxymethylcellulose (CMC 7LFD-type, a cellulose gum, also designated by the tradename Blanose and available from Hercules Chemical Company, 92507, Rueil-Malmaison Ceder, France, 7LFD designating a low viscosity, food grade sodium carboxymethylcellulose having 7 out of 10 glucose units substituted with carboxymethyl group) was mixed in 250l of water and the pH of the solution was adjusted to 5.8 with 15% phosphoric acid and the temperature raised to 40° C. 0.177l of the above-described Trichoderma enzyme preparation, having a total endo-1, 4 beta-glucanase activity of 1,780,000 nkat, was added to the CMC solution. After one hour another 20 kg of CMC was added to the solution. After hydrolysis for 23 hours the enzyme was inactivated by heating (90° C., 15 min.). Finally, the hydrolysis solution was concentrated by spray-drying.

c. CMC Hydrolysate EP151-49

6 kg of sodium carboxymethylcellulose (CMC Finnfix 5, available from Metsä-Serla, Chemical Division, SF-44100 Äänekoski, Finland, representing food grade purity and having a degree of substitution between 0.6–0.8) was mixed with 240l of water. The pH of the solution was adjusted between 5.5 and 5.9 with 15% of phosphoric acid and the temperature was maintained at 40° C. 65 ml of the above-described Trichoderma enzyme preparation, the endo-$\beta$-1,4-glucanase activity of which totalled 539,000 nkat, was added to the CMC solution. After an hour another 6 kg of CMC was added. After hydrolysis for 23 hours, the enzyme was inactivated by heating the solution (90° C., 15 min.). The hydrolysate was then concentrated by spray-drying.

d. CMC Hydrolysate EP151-51

6 kg of sodium carboxymethylcellulose (CMC Finnfix 5) was mixed with 240l of water. Temperature and pH were as described with reference to preparation of EP151-49 (40° C., pH 5.5–5.9). 130 ml of the Trichoderma enzyme preparation, the endo-$\beta$-1,4-glucanase activity of which totalled 1,079,000, was added to the CMC solution. After two hours another 6 kg of CMC was added. After hydrolysis for 47 hours the enzyme was inactivated by heating the solution (90° C., 15 min.). The hydrolysate was then concentrated by evaporating and spray-drying.

e. CMC Hydrolysate EP151-52

This hydrolysate was produced as described with reference to EP151-51, except that 195 ml of the enzyme preparation containing an endo-$\beta$-1,4-glucanase activity of 1,618,000 nkat was used, and the hydrolysis time was 24 hours.

Average DP Calculation

Figure 7:
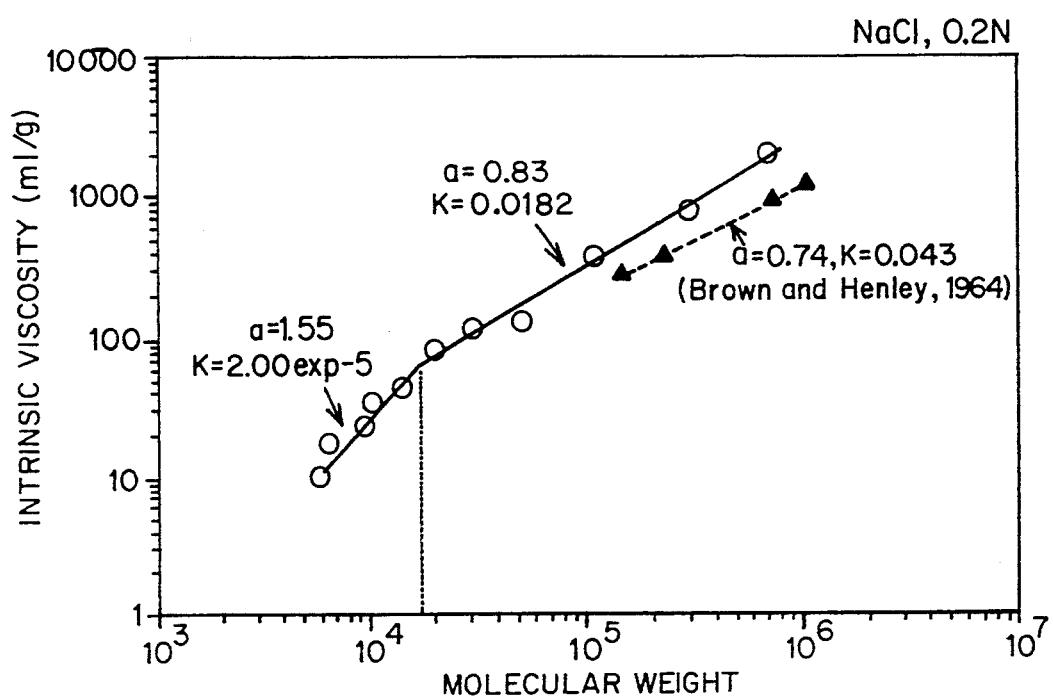
FIG. 7 is a log plot of intrinsic viscosity versus molecular weight as experimentally determined in solid line form for various CMC starting materials (a=0.83, K=0.0182) and hydrolysates (a=1.55, K=2.0 exp −5) in 0.2N solution of NaCl, also showing a dotted line plot for CMC assuming the K and a value for CMC as reported in the literature.

The viscosities, the intrinsic viscosities, the viscosity average molecular weights and the average degrees of polymerization of these various hydrolysate products are set forth in the following Table 3. The average $M_v$ values set forth in Table 3 are calculated values based on the K and a values set forth in the literature reference noted below. The average DP of a polymer or oligomer is calculated by dividing the average molecular weight of the polymer or oligomer by the molecular weight of the monomer (about 220 for CMC). In general, suitable CMC oligomeric mixtures typically have an intrinsic viscosity of between about 50 ml/g and 3 ml/g in 0.2M sodium chloride and a viscosity value between about 5 and about 100 mPas (in 20% by weight solution at 25° C., shear rate $584_s{-1}$. The viscosities were determined using a rotational viscometer (Haake Viscotester VT 500 with sensor system NV, Karlsruhe, Federal Republic of Germany). The intrinsic viscosities were measured according to the conventional method (described in Flory, *Principles of Polymer Chemistry*, Cornell Univ. Press, VII-4a, Ithaca, N.Y. (1953), the contents of which are incorporated by reference) at 25° C. by using a calibrated Cannon Fenske capillary viscometer (size 50, Cannon Instrument, State College, Pa., U.S.A.). Initially approximate viscosity average molecular weights ($M_v$) of certain CMC hydrolysates were determined by measuring the intrinsic viscosity values and using the Mark-Houwink equation:

$$[\eta] = K M_v^a$$

where [$\eta$] is intrinsic viscosity, $M_v$ is the average molecular weight of the polymer and K and a are hydrodynamic constants characteristic of the particular polymer-solvent system. The values of K and a for CMC, which were used in this study, were: K=0.043 in 0.2M NaCl and a=0.74 in 0.2M NaCl as described in the literature reference Brown and Henley, *Studies on Cellulose Derivatives Part IV. The Configuration of the Polyelectrolyte Sodium Chloride Solutions*, Macromol. Chem., Vol. 79, 00. 68–88 (1964) as shown in FIG. 7.

TABLE 3

| CMC Hydrolysate | Viscosity[1] (mPas) | Intrinsic Viscosity[2] (ml/g) | Average $M_v$ | Average DP |
|---|---|---|---|---|
| 151 | 32 | 31.4 | 7400 | 39 |
| 151-2 | 20 | 22.9 | 4800 | 25 |
| 151-49 | 23 | 18.4 | 3600 | 19 |
| 151-51 | 18 | 14.0 | 2500 | 13 |
| 151-52 | 18 | 14.3 | 2600 | 13 |

[1]20% (w/w) solution, 25° C., shear rate = 584 s$^{-1}$
[2]measured in 0.2M NaCl, 25° C.

It is noted that a variety of methods for determining average molecular weight exist, and therefore the values of average molecular weights determined, as well as the average DP values calculated from them, depend upon the experimental method and the basis of calculation. For example, the number average molecular weight can be determined by end group analysis, osmotic pressure, vapor pressure lowering, boiling point elevation, freezing point depression and size exclusion chromatography. The weight average molecular weight can be determined by light scattering experiment, the viscosity average molecular weight from the size exclusion chromatograph. All these methods can be used for determining the average molecular weight which ultimately leads to the average DP values, although different results will be obtained depending on method and calculation used.

The $M_v$ values reported in Table 3 are first estimates obtained using the Mark-Houwink equation and the K and a values reported by Brown and Henley. However, the $M_v$ determined on the basis of the literature value $a=0.74$ for CMC at 0.2N NaCl is higher than the true molecular weight of the CMC hydrolysates listed. Experimental determination of weight average molecular weight ($M_w$) by multi angle light scattering measurement as described below shows that this conventional estimation method based on conventional literature values for k and a is not applicable to low molecular weight or relatively short chain polysaccharide derivative oligomers which are the most preferred embodiments of the invention.

Furthermore, the most preferred oligomeric mixtures according to the invention have a relatively narrow range of molecular weights, i.e. relatively monodispersed, having a polydispersity index ($M_w/M_n$, weight average molecular weight divided by number average molecular weight) of less than about 2.0 and typically less than about 1.8. The weight average molecular weights and number average molecular weights of a variety of CMC hydrolysate samples of different degree of hydrolysis were measured and the polydispersity index of all such hydrolysates was calculated as ranging between about 1.1 and about 1.9. Therefore, the oligomers in a most preferred mixture of oligomers extend over a relatively narrow range of $M_w$ and, even as to mixtures having an average molecular weight at or near the upper limit of $M_w$ where the oligomers may begin to assume a random coil configuration, are comprised of a significant portion, preferably a majority, of oligomers having a rod-like configuration.

In the experimental determination of $M_w$ values as described below, CMC solutions were prepared in 0.2N NaCl solution at pH of 7. The solutions were passed through an HPLC column, and the light intensity was detected by multiangle laser light scattering using a Wyatt Technology, multiangle laser light scattering instrument, model DAWN-F. The flow rate was 0.2 ml/min. The concentrations of the solutions were detected by refractometer, and the sensitivity of the refractometer was 64. The weight average molecular weights, $M_w$, were determined using appropriate computer software.

EXAMPLE 5

Determination of Chain Conformation of CMC Hydrolysates

The following materials were used in the experiments for this study:

I. Sodium Carboxymethyl Cellulose

| Raw Materials: | |
|---|---|
| Samples | Manufacturer |
| Blanose 7HFD | Hercules Chemical Company, France |
| Blanose 7MFD | Hercules Chemical Company, France |
| Blanose 7LFD | Hercules Chemical Company, France |
| Finnfix 5E | Metsa-Serla, Finland |
| Finnfix 2 (Lot No 59135) | Metsa-Serla, Finland |
| Finnfix 2 (Batch 59379-1) | Metsa Serla, Finland |
| Hydrolysates: | |
| Samples | Descriptions |
| 151/70 1 h | hydrolysate of Blanose 7LFD |
| 151/70 2 hrs | hydrolysate of Blanose 7LFD |
| 1511 | hydrolysate of Blanose 7MFD |
| 1512 | hydrolysate of Blanose 7LFD |
| 151/63 1 h | hydrolysate of Blanose 7LFD |
| 151/63 4 hrs | hydrolysate of Blanose 7LFD |
| 151/63 24 hrs | hyrdolysate of Blanose 7LFD |
| 151/47 | hydrolysate of Finnfix 5E |
| 151/51 | hydrolysate of Finnfix 5E |
| 151/46 | hydrolysate of Finnfix 5E |
| 1512 Fr.A | fraction of hydrolysate 1512 |

II. Chemical Reagent Sodium Chloride (Analytical grade, Mallinckrodt, Paris, Ky.).

The chain conformation of the CMC hydrolysates was studied using the Mark-Houwink equation $[\eta]=KM^a$. In the formula, the variable n is instrinsic viscosity, K is a constant indicating the interaction between polymer and solvent, a is the Mark-Houwink exponent and M is the average molecular weight of the polymer. The Mark-Houwink exponent, a, was determined for each hydrolysate for purposes of classifying the oligomer configurations. The average molecular weight of the polymer were measured by multi angle light scattering.

The instrinsic viscosities of the hydrolysates were measured from the concentration dependency of reduced viscosity. The reduced viscosity, specific viscosity divided by concentration of a hydrolysate solution, was determined using a Cannon capillary viscometer. The specific viscosity ($\eta_{sp}$) was calculated using the following formula $$\eta_{sp} = \frac{t}{t_o} - 1$$

wherein t is the flow time of the solution passing through the capillary viscometer and $t_o$ is the flow time of the solvent. The relationship between the reduced viscosity ($\eta_r$) and the concentration (c) is expressed as the following where $[\eta]$ is the intrinsic viscosity:

$$\frac{\eta_{sp}}{c} = [\eta] + k^1 [\eta]c$$

Therefore, the intrinsic viscosity was calculated by plotting the measured reduced viscosity versus various concentrations of hydrolysate solutions and the intercept of the plot at concentration of zero was the intrinsic viscosity of the hydrolysates tested.

The Mark-Houwink exponent, a, and the constant, K, of the Mark-Houwink equation, $[\eta] =KM^a$, were determined for various CMCs such as listed in Table 5 (in solutions of varying concentration of NaCl) by plotting the log $[\eta]$ versus the log of weight average molecular weight, $M_w$ (e.g. FIG. 7). $M_w$ was experimentally determined by multi angle light scattering instrument measuring as described above. The slope of the plot log $[\eta]$ versus log [$M_w$] provides the exponent value a and the intercept of the plots at a theoretical log [$M_w$] of zero provides the value K. The a and K values thus determined are set forth in Table 4.

Chain Conformation

Figure 11:
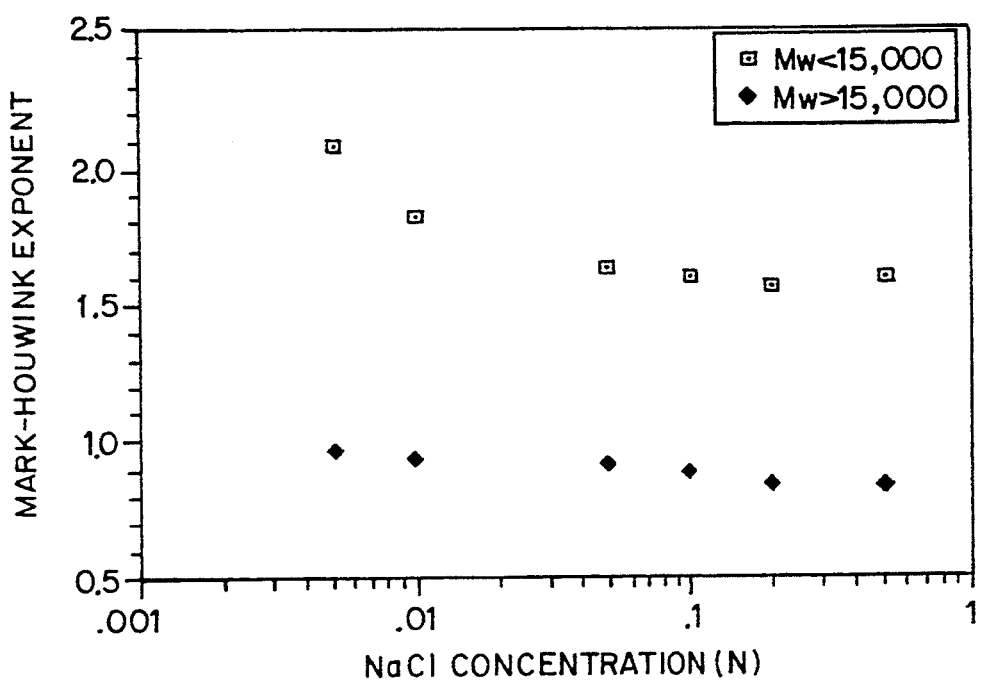
FIG. 11 is a plot of the Mark-Houwink exponent versus the NaCl concentration of CMC raw materials (◆) and CMC hydrolysates (□).

The dependency of Mark-Houwink exponent on differences in salt concentration showed the difference between CMC raw materials and hydrolysates (Table 4 and FIGS. 7 and 11). The Mark-Houwink exponents for CMC raw materials (having $M_w$ greater than about 15,000) are 0.97, 0.94, 0.91, 0.88, 0.83 and 0.83 at NaCl concentrations of 0.005, 0.010, 0.050, 0.100, 0.200 and 0.500N, respectively. In contrast, the Mark-Houwink exponents for CMC hydrolysates (having $M_w$ less than about 15,000) are 2.07, 1.82, 1.63, 1.59, 1.55 and 1.58 at NaCl concentrations of 0.005, 0.010, 0.050, 0.100, 0.200 and 0.500N, respectively. These values are approximately twice (2.13, 1.94, 1.79, 1.81, 1.87, 1.90 times) higher than those of CMC raw materials. The Mark-Houwink exponents of CMC raw materials decreased 14% over the NaCl concentration of 0.005N to 0.50N, while those of hydrolysates decreased 24% over the same range. Therefore, the decrease in the hydrolysates is 1.7 times higher than the CMC raw materials. Mark-Houwink exponents become a constant when the NaCl concentration is higher than 0.2N, probably having reached the unperturbed condition.

Figure 6:
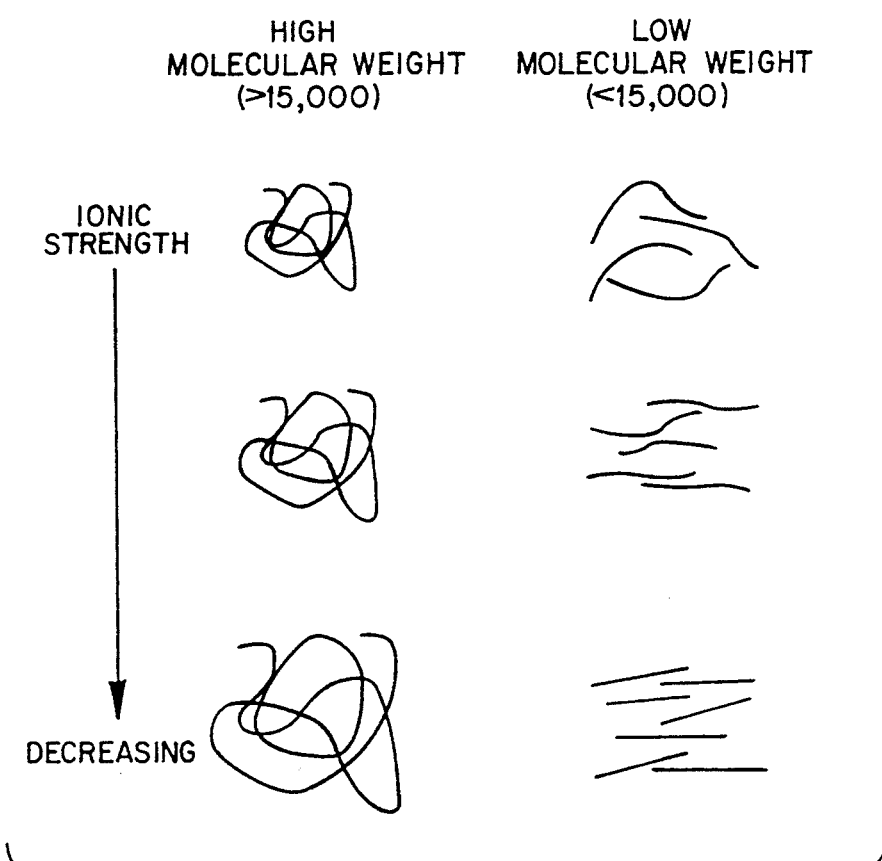
FIG. 6 shows the molecular weight dependent conformation transition in CMC (for both CMC raw materials, $M_w > 15,000$, which are used as starting materials to obtain certain hydrolysates described and CMC hydrolysates, $M_w < 15,000$)

The Mark-Houwink exponents of 0.83–0.97 for CMC raw material (Mw>15,000 Daltons) indicate a free draining random coil conformation (left hand column of FIG. 6). In the random coil conformation, polymer coils are confined by the intra-chain interactions, therefore less change is seen in the Mark-Houwink exponent within the same range of ionic strength. However, when the weight average molecular weight is less than 15,000 Daltons, the CMC chain is not sufficiently long to form a winding coil, the polymer chain is no longer subjected to the constraint of intra-chain interactions, and a chain of free strip or rod-like configuration may form (right hand column of FIG. 6). When the ionic strength is low, the electrostatic repulsion force becomes dominant due to the negative charge of the carboxymethyl groups, and the polymer assumes its most stiff rod-like conformation with the highest value of the Mark-Houwink exponents (Table 4 and FIG. 6). When the ionic strength increases, the negative charge of carboxymethyl groups is shielded, the repulsion forces between the neighboring groups are reduced, and the polymer chains relax, yielding a lower Mark-Houwink exponent (Table 4 and FIG. 6).

The experimentally determined data, as described herein, and with reference to FIGS. 6–11, thus shows that the molecular weight and chain conformational characteristics of the most preferred polysaccharide derivative oligomeric mixtures of the invention, i.e. mixtures comprising a significant or substantial portion of oligomers of rod-like conformation, are distinctly different from polysaccharide polymer compositions previously known or employed in any application. Current understanding of the unique nature and properties of the relatively low molecular weight or short chain oligomers of the most preferred oligomeric mixtures of the invention is lacking. As shown by the experimentally determined Mark-Houwink a values listed in Table 4 for weight average molecular weights, $M_w$, of CMC at less than about 15,000 daltons (a=1.58 to 2.07), the literature value of a=0.74 for CMC is erroneous with respect to CMC having a $M_w$ of less than about 15,000 daltons. This experimentally determined data quantitatively indicates that relatively short chain CMC assumes a rod-like configuration (right hand column of FIG. 6) as opposed to a free draining random coil conformation (left hand column of FIG. 6).

TABLE 4

| NaCl Concentration (N) | Mark Houwink Equations for CMC (25° C.) | |
|---|---|---|
| | Weight Average Molecular Weight | |
| | >15,000 | <15,000 |
| 0.005 | $[\eta] = 0.0069 M_w^{0.97}$ | $[\eta] = 0.02 \times 10^{-5} M_w^{2.07}$ |
| 0.010 | $[\eta] = 0.0084 M_w^{0.94}$ | $[\eta] = 0.17 \times 10^{-5} M_w^{1.82}$ |
| 0.050 | $[\eta] = 0.0090 M_w^{0.91}$ | $[\eta] = 0.83 \times 10^{-5} M_w^{1.63}$ |
| 0.100 | $[\eta] = 0.0116 M_w^{0.88}$ | $[\eta] = 1.18 \times 10^{-5} M_w^{1.59}$ |
| 0.200 | $[\eta] = 0.0182 M_w^{0.83}$ | $[\eta] = 2.00 \times 10^{-5} M_w^{1.55}$ |
| 0.500 | $[\eta] = 0.0179 M_w^{0.83}$ | $[\eta] = 1.21 \times 10^{-5} M_w^{1.58}$ |

Chain Stiffness Parameter

Figure 8:
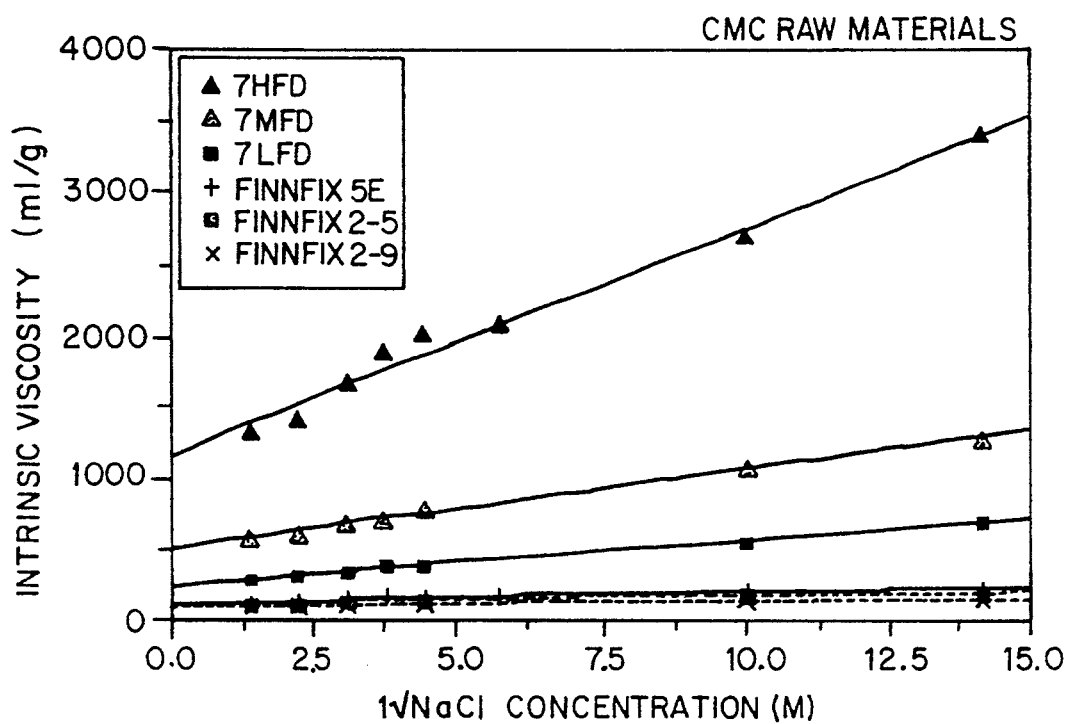
FIG. 8 is a plot of the intrinsic viscosity versus the square root of NaCl concentration of the CMC raw materials.
Figure 9:
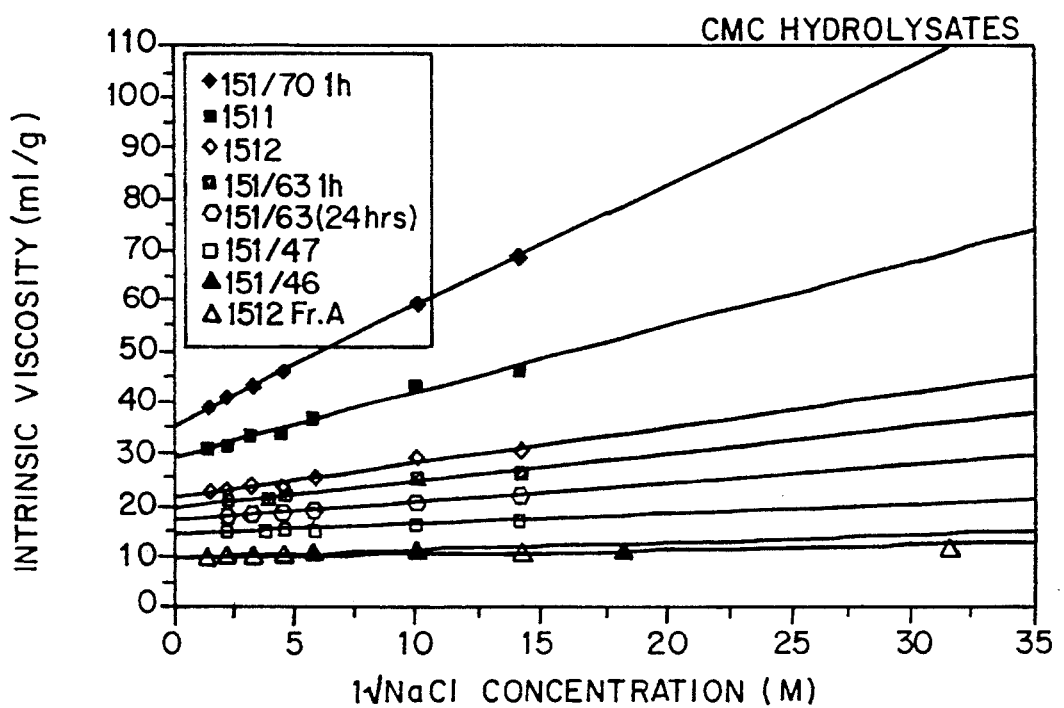
FIG. 9 is a plot of the intrinsic viscosity of the CMC hydrolysates versus the square root of the NaCl concentration.
Figure 10:
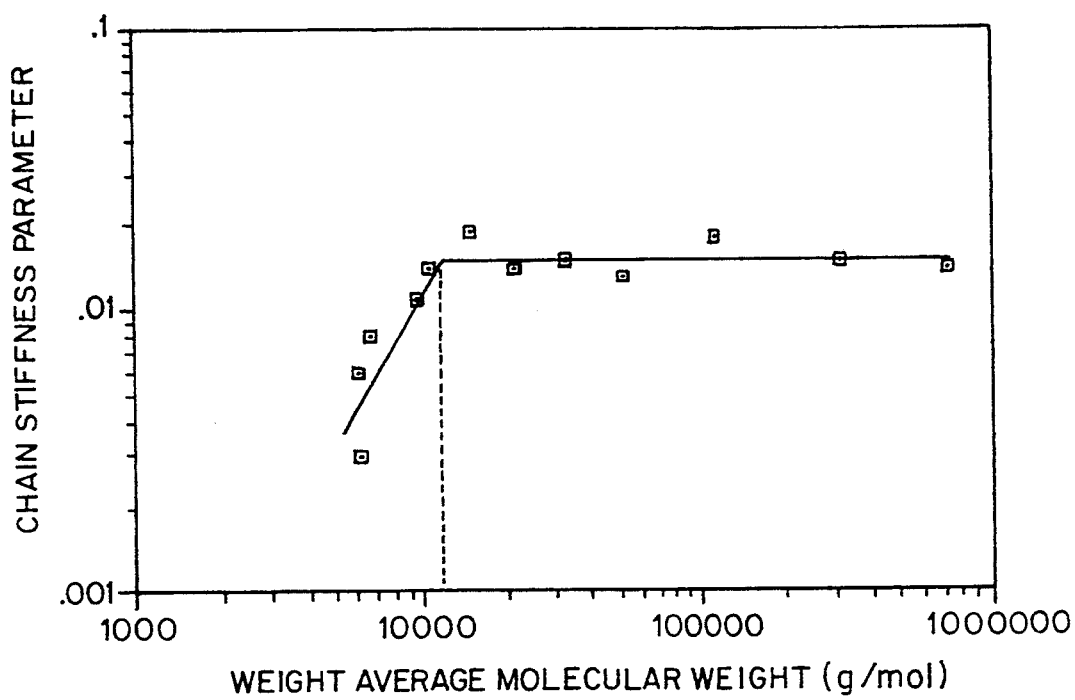
FIG. 10 is a log plot of the chain stiffness parameter versus the weight average molecular weight of CMC showing a transition occurring at a lower molecular weight.

The chain stiffness parameters are 0.014, 0.015, 0.018, 0.013, 0.015, 0.014, 0.019, 0.014, 0.011, 0.010, 0.008, 0.005, 0.006 and 0.003 for Blanose 7HFD, Blanose 7MFD, Blanose 7LFD, Finnfix 5E, Finnfix 2 (Lot# 59135), Finnfix 2 (Batch 59379-1), 151/70 1 h, 1511, 1512, 151/63 1 h, 151/63 24 hrs, 151/47, 151/46 and 1512 Fr.A, respectively (Table 4). These chain stiffness parameters were calculated from the slopes of the plot between the intrinsic viscosity and the square root of NaCl concentration (FIG. 8 and FIG. 9). The relationship between the chain stiffness parameter and the weight average molecular weight shows a sudden decrease in the chain stiffness parameter when the weight average molecular weight becomes less than 10,000 Daltons (FIG. 10). This confirms that the conformational transition occurs, and low molecular weight CMC or CMC hydrolysate becomes significantly more stiff compared with higher molecular weight CMC. As shown repeatedly, ordinary CMC follows Gaussian chain distribution and behaves as a free draining random coil with Mark-Houwink exponents varying from 0.83–0.97. Upon hydrolysis, the low molecular weight CMC chain is no longer able to turn and the back bone forms a free strip, thereby relieving the intra-chain interactions (FIG. 6). Consequently, the conformation of the short chain corresponds to a rod-like shape with Mark-Houwink exponents varying from 1.2 to 2.0 and also results in the lower value of chain stiffness parameters. Experimental results (Table 5) show some deviation in the values of the chain stiffness parameter for higher molecular weight CMC. This may be due to the differences in the molecular weight distributions.

TABLE 5

The Chain Stiffness Parameter of CMC and CMC Hydrolysates

| CMC | Mw | Chain Stiffness Parameter (B) |
|---|---|---|
| Raw Materials | | |
| 7HFD | 687,500 | 0.014 |
| 7MFD | 292,700 | 0.015 |
| 7LFD | 108,600 | 0.018 |
| Finnfix 5E | 50,200 | 0.013 |
| Finnfix 2 Lot #59135 | 30,700 | 0.015 |
| Finnfix 2 Batch 59379-1 | 20,200 | 0.014 |
| Hydrolysates | | |
| 151.70 1 h | 14,400 | 0.019 |
| 1511 | 10,400 | 0.014 |
| 1512 | 9,400 | 0.011 |
| 151/63.1 hr. | — | 0.010 |

TABLE 5-continued

The Chain Stiffness Parameter of CMC and CMC Hydrolysates

| CMC | Mw | Chain Stiffness Parameter (B) |
|---|---|---|
| 151/63.24 hrs | 6,500 | 0.008 |
| 151/47 | — | 0.005 |
| 151/46 | 5,800 | 0.006 |
| 1512 Fr.A | 6,000 | 0.003 |

Food Formulations

As discussed in several exemplary food formulations herein which employed conventional polysaccharide compositions (not containing a significant portion of rod-like oligomers) as a fat replacer (e.g. non-degraded CM starch or a commercially available maltodextrin as a fat replacer in a butter icing formulation), the resulting food formulations were unsatisfactory.

Madeira Cake

Following is a conventional ingredient recipe (representing a total batch weight) and method for making a Madeira cake having normal levels of sugar, fat and/or carbohydrate:

| Ingredients | Weight (g) |
|---|---|
| High ratio cake flour | 200 |
| Sugar caster (sweetener) | 250 |
| High ratio shortening | 130 |
| Skimmed milk powder | 16 |
| Salt | 3 |
| Baking powder (raising agent) | 12 |
| Water | 180 |
| Egg | 176 |

METHOD (using Hobart Laboratory Mixer)
1. Place water, dry ingredients and fat in the bowl
2. Using beater, mix on speed 1 for 30 secs and scrape down
3. Mix on speed 3 for another 30 secs and scrape down
4. Add egg over 30 secs on speed 1 and scrape down
5. Mix on speed 2 until 0.8 specific gravity is obtained
6. Scale 180 g into greased tins and bake at 170° C., middle shelf of domestic fan oven for 30 mins.

Utilizing various aqueous solutions of EP151, EP151-2, EP151-49, EP151-50 and EP151-51 of varying concentrations (and therefore, varying viscosity), 40% of the normal high ratio shortening (or fat) ingredient, i.e. 52 g of fat or 5.4% of the total batch weight of the above Madeira cake recipe, was replaced with the following listed solutions in an amount so as to achieve a level of dry EP151, EP151-2, EP151-49, EP151-51 or EP151-52 ingredient as listed below (expressed as level of dry ingredient used as a percentage of total batch weight):

| CMC Hydrolysate Substitute (% by weight in aqueous solution) | Level of fat substitution (% of fat wt) | Level of fat substitution (% of total batch wt) | Level of dry ingredient used (% of total batch wt) |
|---|---|---|---|
| EP151 (40% solids) | 40% | 5.4% | 2.2% |
| EP151-2 (47% solids) | 40% | 5.4% | 2.5% |
| EP151-2 (40% solids) | 40% | 5.4% | 2.2% |
| EP151-49 (46% solids) | 40% | 5.4% | 2.5% |
| EP151-49 (40% solids) | 40% | 5.4% | 2.2% |
| EP151-51 (50% solids) | 40% | 5.4% | 2.7% |
| EP151 51 (40% solids) | 40% | 5.4% | 2.2% |
| EP151-51 (50% solids) | 40% | 5.4% | 2.7% |
| EP151-52 (40% solids) | 40% | 5.4% | 2.2% |

All of the Madeira cakes produced according to the above-listed substitutions had acceptable appearances, colors, volumes, textures, structures, odors, flavors and mouthfeels. The water activities of the various cakes differed slightly due to the slightly varying amounts and concentrations of the solutions substituted. Preparations wherein about 40% to about 75% of the fat ingredient is replaced with a substantially equivalent weight amount of a 40% solution of EP 151-51, should produce relatively acceptable cakes. Thus, it is believed that acceptable cakes may be obtained somewhere at a level of 40%–75% fat replacement with a degraded cellulose derivative mixture of oligomers (average DP 5–500).

As is known in the art with regard to cake mixtures of the sort similar to the specific Madeira cake formulation set forth above, the amount of the major ingredients comprising more than about 10% of the total batch weight, may be varied by about plus or minus 5%, and the ingredients comprising less than about 10% of the total batch weight might typically be varied by about plus or minus 1%. With regard to cake mixtures generally (i.e. other than Madeira cake), flour, sugar (sweetener), shortening (fat), baking powder, water and egg components are typically common to all.

Butter Icing (Frosting)

Following is a conventional ingredient recipe (representing a total batch weight) and method for making a butter icing having normal levels of fat:

| Ingredients | Weight (g) |
|---|---|
| Butter (unsalted) | 179 |
| Icing sugar (sweetener) | 225 |
| Water | 96 |

METHOD
1. Soften the butter
2. Add icing sugar and cream together
3. Add water slowly and whisk until light and fluffy.

Again utilizing various solutions of EP151, EP151-2, EP151-49, EP151-51 and EP151-52 of varying concentrations, 33% of the fat (butter) ingredient, i.e. 60 g or 11.8% of the total batch weight, was replaced with the following listed solutions wherein the following listed amounts of solid EP151, EP151-2, EP151-49, EP151-51 and EP151-52 were added (expressed as level of dry ingredient used as % of total batch weight):

| CMC Hydrolysate Substitute (% by weight of aqueous solution) | Level of fat substitution (% of fat wt) | Level of fat substitution (% of total batch wt) | Level of dry ingredient used (% of total batch wt) |
|---|---|---|---|
| EP 151 (40% solids) | 33% | 11.8% | 4.7% |
| EP 151-2 (47% solids) | 33% | 11.8% | 5.5% |
| EP 151-2 (40% solids) | 33% | 11.8% | 4.7% |
| EP 151-49 (46% solids) | 33% | 11.8% | 4.7% |
| EP 151-49 (40% solids) | 33% | 11.8% | 4.7% |
| EP 151-51 (50% solids) | 33% | 11.8% | 5.9% |
| EP 151-51 (40% solids) | 33% | 11.8% | 4.7% |
| EP 151-51 (50% solids) | 33% | 11.8% | 5.9% |
| EP 151-52 (40% solids) | 33% | 11.8% | 4.7% |

All of the butter icings obtained via the above-listed levels of fat replacement were acceptable. Although these icings had slightly higher bulk densities relative to an icing obtained from a conventional recipe, the eating quality was not substantially affected. At 40% fat replacement with EP151-52 a better product was obtained than might be obtained via replacement of the fat with conventional fat sparing agents such as potato maltodextrin. Preparations in which about 30% to about 75% of the fat ingredient of the conventional recipe is substituted with an equivalent weight amount of a 40% solution of EP151-52 should produce relatively acceptable icings. Thus, a butter icing in which about 30% to about 75% of the fat ingredient is replaced with a degraded cellulose derivative oligomeric mixture having an average DP of between about 3 and about 300 produces a low calorie icing of acceptable eating quality. Where greater than about 50% fat replacement is desired, appropriate amounts of a stabilizer and/or an emulsifier should also preferably be included in the recipe.

As is known in the art, the tolerance range for variation of the various components in the typical icing formulation set forth above is plus or minus about 5%.

Mayonnaise

With respect to attempting to obtain a fat substituted low calorie mayonnaise product, the following is an already low calorie (fat reduced) recipe which might be modified by replacing a portion of the water and starch components of the low calorie recipe with an equivalent amount (by weight) of a solution of a degraded cellulose derivative.

| Ingredients | Weight (g) |
|---|---|
| Water | 243.0 |
| Vegetable oil | 180.00 |
| Instant starch (thickener) | 27.0 |
| White vinegar (acidifier) | 84.0 |
| Egg Yolk (emulsifier) | 48.0 |
| Salt | 9.0 |
| Powdered glucose | 9.0 |

METHOD
1. Blend all the dry ingredients and add slowly to the water which is being whipped on a Hobart at medium speed.
2. Heat the solution to 60° C.
3. Cool to 20° C.
4. Add the egg yolk and mix well.
5. Add the chilled oil (10° C.) slowly while agitating on the Hobart on medium speed.
6. When most of the oil is added, add vinegar slowly while mixing.

By way of example, one modified reduced calorie recipe of acceptable eating quality was obtained by replacing 54 g of the water and 27 g of the starch ingredients of the above mayonnaise recipe with an equivalent amount by weight of a 40% solution of EP151. EP151 may be incorporated into the above reduced calorie recipe up to at least about 15% of the total batch weight. A normal fat containing mayonnaise recipe typically includes about 2.5 times as much fat (vegetable oil) as the above recipe. Thus, an acceptable low fat mayonnaise can be obtained by replacing from about 25% to about 75% of the fat components with water and an appropriate amount of a degraded cellulose derivative mixture of oligomers having an average DP of between about 3 and about 300.

As is known in the art, mayonnaise formulations generally include at least water, vegetable oil (fat), vinegar (acidifier) and egg yolk (emulsifier); and the major components, water and fat, have a tolerance level of variation of plus or minus about 5%, and the minor components have a tolerance variation level of plus or minus about 1%.

Spreads

With respect to attempting to obtain a fat-reduced spread of better quality, the water component of the following already low fat spread recipe (representing a total batch weight) was modified by substituting a selected amount of a 50% solution of EP151-52 therefor.

| Ingredients | Weight (g) |
|---|---|
| Soft margarine blend (fat) | 234.0 |
| Dimodan CP (Emulsifier) | 6.0 |
| Water | 350.4 |
| Salt | 3.6 |
| Sobalg FD120 (Stablilizer) | 6.0 |

METHOD
1. Melt the fat blend and dissolve Dimodan CP into it. Heat to 50° C.
2. Dissolve the salt and Sobalg FD120 into the aqueous phase and heat to 50° C.
3. Place the warm fat phase in a large plastic beaker and insert the large paddle of the motor stirrer.
4. Add the aqueous phase to the fat phase slowly and gradually while stirring at a medium speed. Enough stirring is required to get a good dispersion, but care must be taken to ensure no air is drawn into the mixture.
5. Put the freezing unit of the ice cream maker on for 10 minutes before adding the emulsion.
6. Freeze down for 15 minutes, transfer into plastic tubs and immediately place in a constant temperature 5° C. room.

Various levels of EP151-52 solution addition were tested by replacing 12 g (2% of total batch weight) 60 g (10% of total batch weight), and 120 g (20% of total batch weight) of the water component in the above-listed low fat recipe with an equivalent amount by weight of a 50% solution of EP151-52. Up to 20% of total batch weight replacement (i.e. up to 120 g) produced a low fat spread of acceptable eating quality. At about 20% total batch weight replacement, the EP151-52 containing low fat spread was better than the recipe above.

Normal fat containing spread typically includes about 79–83% of fat and about 16–20% water (as opposed to the above-listed low fat spread recipe wherein the fat phase is about 25–40% and water is about 58–75% water). Thus an acceptable low fat spread can be obtained by replacing from about 38% to about 75% of the fat components (typically butter and/or vegetable oils) in a normal fat containing margarine spread with water and an appropriate amount of a degraded cellulose derivative mixture of oligomers having an average DP of between about 5 and about 500. According to the above-described modification and improvement of the already low fat recipe, a normal fat spread recipe can thus suitably be modified by replacing from 38%–75% of the fat component with an equivalent amount by weight of an aqueous solution containing from about 3% to about 70% degraded cellulose derivative, and more preferably, a solution containing from about 30% to about 50% of degraded cellulose derivative material.

As is known in the art, all low fat spread formulations generally include at least fat blend, water, emulsifier and stabilizer ingredients; and, these various major components typically have a tolerance variation level of plus or minus about 1%.

Preparation of a Maize Meal Snack Containing a CMC Hydrolysate

An expanded snack product based on maize meal and potato granules and containing cheese powder and flavour was produced in accordance with the following standard formulation:

| | |
|---|---|
| Maize meal | 72.5% |
| Potato granules | 10.0% |
| Oat bran | 5.0% |
| Castor sugar | 1.0% |
| Cheese powder | 8.0% |
| Cheese flavour | 2.0% |
| Salt | 1.5% |

A CMC hydrolysate produced in the manner described above, more particularly as described for hydrolysate EP151-52, was incorporated at levels from 0.05 to 5%, preferably 1 or 2%, by weight of the total formulation.

The snacks were produced by extrusion and cooked at 100° C. during the extrusion process. Comparison of the products containing 1 or 2% of the cellulose derivative with those containing none of the cellulose derivative showed that the former had a lighter structure, and crisper and crunchier texture produced without frying, and less stickiness.

The Preparation of a Batter Mix Containing a CMC Hydrolysate

A standard batter mix formulation was made from the following ingredients:

| | |
|---|---|
| Wheat flour | 42.0% |
| Water | 57.0% |
| Salt | 1.0% |

These ingredients were mixed together and whisked to produce a uniform batter. The cellulose derivative (as in Example 5) was incorporated at a level of 1, 2 or 5% by weight to replace the corresponding amount of the flour.

The batter was used to coat mushrooms which were then fried at 170° C. It was found that the standard frying time of 10 minutes (in the absence of the cellulose derivative) was reduced to 8 minutes by the presence of 1% cellulose derivative, to 6 minutes by the presence of 2% cellulose derivative, and to 4 minutes by 5% of the cellulose derivative.

The fried mushrooms produced with the batter in accordance with the present invention showed greater water retention and hence higher weight and lower fat uptake. They maintained their crispness for longer and had improved appearance and customer acceptability. Moreover, the oil used for the frying had a longer life.

Marzipan

Following is a conventional recipe (representing total batch weight) and method for making marzipan:

| Ingredients | Weight (g) |
|---|---|
| Icing sugar (carbohydrate) | 21.8 g |
| Caster sugar (carbohydrate) | 21.8 g |
| Ground Almonds | 43.7 g |
| Vanilla Flavoring | 0.8 g |
| Egg | 10.9 g |
| Lemon Juice | 0.8 g |

The above mixture is formed into a ball, lightly kneaded, rolled out and cut into desired shapes.

Up to about 40% of the icing sugar component may be replaced with an appropriate amount of a degraded cellulose derivative having an average DP of 3–500 and a confection of acceptable eating quality obtained.

Other Foodstuffs

Apart from sweet and savoury food products such as cake, icing, cookies, spreads, creams, snack fillings and the like, the degraded cellulose derivatives of the invention should be suitable as high calorie component (fat, carbohydrate) substitutes in relatively high protein containing systems such as meat pate and other meat emulsions, it being recognized that for any given foodstuff composition, the particular range of amounts of certain ingredients of the normal high calorie recipe which may be modified to allow a degraded cellulose derivative to be incorporated, is determined to provide an end food product which has an eating quality approaching that of the normal high calorie recipe.

General Preparation of a Typical Starch Derivative Hydrolysate

A most preferred starch derivative for use herein is carboxymethyl starch. The invention is not limited to the use of this polysaccharide derivative, but others, such as hydroxypropyl, methylethyl, hydroxyethyl and other typically lipophilic functional group substituted starches may be more suitable for a specific application.

In one embodiment of the invention, starch derivative hydrolysates may be prepared from starch derivatives as defined above by an enzymatic hydrolysis utilizing an amylolytic preparation having alpha amylase as the main active hydrolytic agent such that only insignificant amounts of mono- and disaccharides are produced.

Enzymes which may be used in some embodiments of this invention, e.g. with respect to starch derivatives, are various food-grade amylolytic enzyme preparations. They can be produced from a multitude of different microorganisms such as strains of Bacillus, Klebsiella, Clostridium, Aspergillus, Rhizopus. Typical commercially available enzyme preparations suitable for use herein are amylolytic preparations (such as alpha and beta amylases), pullulanases, and cyclodextrin glycosyltransferases (CGTase).

The hydrolysis procedure is generally carried out by dissolving the starch derivative in water, adjusting the pH and the temperature to the value suitable for the enzyme activity, adding the enzyme to the solution and allowing the enzyme to react for a suitable time. After the reaction, the enzyme is inactivated by heating the solution up to about 100° C. and the hydrolysate product is concentrated and dried. The average degree of polymerization (DP) of the polymers formed by such a hydrolysis may be less than 500 as determined by reducing end group measurement according to Somogyi, M. J., *Biol. Chem.* 195, 19-33 (1952). The specific conditions suitable for and the specific time sufficient to secure the desirable hydrolysis may be readily determined for each selected starch derivative and each selected enzyme preparation.

Similarly in other embodiments of the invention where degradation is carried out using chemical or physical means, the average DP of the polymers is less than 500. Most preferably in such embodiments, the treatment conditions are selected such that the resulting polymeric mixtures contain less than about 25%, and most preferably less than about 10%, by weight of mono- and disaccharides.

Use of Oligomeric Mixtures Derived from Starch Derivatives in Food Applications

The degraded starch derivative products of the invention dissolve or suspend rapidly in water and are physiologically inert.

The calorie content of carbohydrates in general is 4 kcal/g, which as such is less than the caloric content of fats (9 kcal/g). Carboxymethyl starch is an ether type starch, and it has been suggested that ether linkages with respect to the derivative in starch are not hydrolysable (*Food Technology Review*, No. 52, 1979, p. 113). Thus the calorie content of CM starch and its hydrolysates may be even less than 4 kcal/g. According to U.S. Pat. No. 3,505,110, another ether type starch, namely hydroxypropylated starch was hydrolysed to a syrup that was found to be amylase resistant. Thus the caloric value of the product was very low, and it was suggested to be used as a substitute for ordinary sugars. Similarly, the calorie content of various polysaccharides with various functional groups such as carboxymethyl starch are believed to be very low and certainly less than the original polysaccharide or its degraded forms.

The following examples set forth typical exemplary routines for preparing a starch and various starch derivatives hydrolysates therefrom.

EXAMPLE 6

Starch Derivative Enzymatic Hydrolysis 60 g of carboxymethyl starch (CM starch) derived from potato starch (Primojel; Avebe, 9607 PT Foxhol, The Netherlands) was mixed in 1200 ml of water. The temperature of the mixture was raised to 80° C. and the suspension was mixed continuously. 1.5 ml of amylase (Ban 120L, Novo, Industri A/S, Novo Alle, 2880 Bagsvaerd, Denmark) dilution 1/50 by volume was added to the suspension mixture. After hydrolysis of about 30 minutes the enzyme was inactivated by heating (100° C., 10 min.). The hydrolysate was then freeze-dried.

The hydrolysate contained negligible amounts of glucose, maltose and oligosaccharides, as the value of reducing sugars was 0.28%. The viscosity of a 5% by weight suspension of the hydrolysate (measured using Haake-Rotovisco RV 12 viscometer with sensor systems NV; Karlsruhe, Federal Republic of Germany) at 25° C. was 57 mPa.s (using the shear rate of 692 1/s). The viscosity of the unhydrolysed raw CM starch material was 106 mPa.s (25° C., 692 1/s). Since the viscosity of the hydrolysates is much lower, the hydrolysates can be used at much higher concentration than the original high molecular weight starch derivatives.

Preparation of Butter Icing Using CM Starch Hydrolysate

A butter icing was prepared with the carboxymethyl starch (CM starch) hydrolysate of Example 5 to replace 33% of the normal fat content of a conventional butter icing recipe. The butter icing contained the following ingredients:

| Butter (Fat) | 120 g | 24% |
| --- | --- | --- |
| CM starch hydrolysate (15% by weight suspension in water) | 59 g | 12% |
| Icing sugar | 225 g | 45% |
| Water | 96 g | 19% |

The CM starch hydrolysate was added to the soft butter, while whisking with electric hand whisk. After that the icing sugar was added. Finally water was added slowly and whisking was continued until the emulsion was light and even.

The resultant butter icing had a good, even texture and a pleasant mouthfeel.

In the recipe above, the butter (fat) content would normally be about 180 g.

Preparation of Butter Icing Non-Degraded CM Starch

A butter icing was prepared with non-degraded high molecular weight carboxymethyl starch (CM starch) to replace 33% of the normal fat content. The butter icing contained the following ingredients:

| Butter | 120 g | 24% |
| --- | --- | --- |
| CM starch (5% by weight suspension in water) | 59 g | 12% |
| Icing sugar | 225 g | 45% |
| Water | 96 g | 19% |

The high molecular weight CM starch suspension was added to the soft butter, while whisking with electric hand whisk. After that the icing sugar was added. Finally water was added slowly while still whisking.

No emulsion was formed, but water and oil were immediately separated resulting in an unsuitable food product. When a 10% suspension of non-degraded CM starch was used instead of 5% suspension, the same result was obtained.

Preparation of Butter Icing Using Maltodextrin

A commercial maltodextrin was used to replace 33% of the normal fat content in butter icing. This maltodextrin is manufactured by enzymatic hydrolysis of potato starch and has been recommended to be used as a fat replacer, e.g. in mayonnaises, salad dressings, spreads and fillings. The butter icing contained the following ingredients:

| Butter | 120 g | 24% |
|---|---|---|
| Maltodextrin (25% by weight suspension in water) | 59 g | 12% |
| Icing sugar | 225 g | 45% |
| Water | 96 g | 19% |

The maltodextrin suspension was added to the soft butter, while whisking with electric hand whisk. The icing sugar was subsequently added. Finally the water was added slowly while still whisking.

The resultant icing curdled and was very unstable.

Preparation of Madeira Cake Using CM Starch Hydrolyzate

The CM starch hydrolysate of Example 5 was used to replace 40% of the normal fat content in a Madeira cake recipe containing the following ingredients:

| Cake Flour | 100 g | 21% |
|---|---|---|
| Sugar caster | 125 g | 26% |
| Butter | 39 g | 8% |
| CM starch hydrolysate (15% by weight suspension) | 26 g | 5% |
| Skimmed milk powder | 8 g | 2% |
| Baking Powder | 6 g | 1% |
| Salt | 1.5 g | 0.3% |
| Water | 90 g | 19% |
| Egg | 88 g | 18% |

The normal butter content in the above recipe is 65 g. The dry ingredients were mixed in a bowl. The water, fat and the CM starch hydrolysate were added. Using an electric hand whisk, the mixture was mixed on speed 1 (lowest speed) for 30 seconds and on speed 3 (highest speed) for 30 seconds. The egg was then added over 30 seconds on speed 1 and mixing was continued on speed 2 for 135 seconds. Batter was poured into greased tins and baked at 170° C. for about 35 minutes.

The modified cake was evaluated and compared with a full fat Madeira cake. The standard cake had slightly more coarse crumb than the modified cake, with 40% fat replaced by CM starch hydrolysate. Both cakes were found to have a pleasant appearance, taste and mouthfeel.

Partial Replacement of Normal Fat Content in Butter

The CM starch hydrolysate the production of which is described in Example 5 was used to replace 33% of the normal fat content in a conventional butter by mixing 10 g of conventional butter with 5 g of CM starch hydrolysate (15% by weight suspension in water). A good shiny and stable emulsion was formed similar to butter.

EQUIVALENTS

Those skilled in the art will be able to ascertain, using no more than routine experimentation, many equivalents of the specific embodiments of the invention described herein.

These and all other equivalents are intended to be encompassed by the following claims.

We claim:

1. A foodstuff composition comprising: a first fat or carbohydrate ingredient, wherein between about 1 and about 100% of the first ingredient is replaced with an enzymatically degraded product of a cellulose derivative consisting essentially of a mixture of oligomers of the cellulose derivative a majority of said oligomers having an average DP of between about 5 and about 50.

2. A foodstuff composition as claimed in claim 1 wherein the first ingredient is a fat ingredient.

3. A foodstuff composition as claimed in claim 1 wherein the first ingredient is a carbohydrate ingredient.

4. A foodstuff composition as claimed in claim 1 wherein the cellulose derivative is selected from the group consisting of carboxymethyl cellulose, methyl cellulose, hydroxypropyl cellulose, methylethyl cellulose, hydroxypropylmethyl cellulose, hydroxymethylethyl cellulose and mixtures thereof.

5. A foodstuff composition as claimed in claim 4 wherein the cellulose derivative is carboxymethyl cellulose.

6. A foodstuff composition as claimed in claim 5 wherein the oligomers of the degradation product have an average molecular weight of less than about 15,000 daltons.

7. A foodstuff composition as claimed in claim 1 wherein the degradation product has sufficient water solubility to provide solutions containing at least about 40 weight percent solids.

8. A foodstuff composition as claimed in claim 1 wherein the degradation product has a viscosity of less than about 33 milli-pascals-second in a 20 percent by weight solution.

9. A foodstuff composition as claimed in claim 7 wherein the cellulose derivative is selected from the group consisting of carboxymethyl cellulose, methyl cellulose, hydroxypropyl cellulose, methylethyl cellulose, hydroxypropylmethyl cellulose, hydroxymethyethyl cellulose and mixtures thereof.

10. A foodstuff composition as claimed in claim 9 wherein the cellulose derivative is carboxymethyl cellulose.

11. A foodstuff composition as claimed in claim 2 wherein the degradation product has a sufficient water solubility to provide solutions containing at least about 40 weight percent solids.

12. A foodstuff composition as claimed in claim 11 wherein the cellulose derivative is selected from the group consisting of carboxymethyl cellulose, methyl cellulose, hydroxypropyl cellulose, methylethyl cellulose, hydroxypropylmethyl cellulose, hydroxymethyl cellulose and mixtures thereof.

13. A foodstuff composition as claimed in claim 12 wherein the cellulose derivative is carboxymethyl cellulose.

14. The foodstuff composition of claim 1 wherein between about 1% and about 70% of the first ingredient is replaced with the enzymatically degraded product.

* * * * *